US009284560B2

(12) United States Patent
Zhu et al.

(10) Patent No.: US 9,284,560 B2
(45) **Date of Patent: *Mar. 15, 2016**

(54) APPLICATION OF HIGHLY CONSERVED DOMAIN SEQUENCES FROM VIRAL GENOME AS TEMPLATE TO DESIGN THERAPEUTIC SLIRNAS

(75) Inventors: York YuanYuan Zhu, Palo Alto, CA (US); Li Chen, Nantong (CN); Tiejun Li, Nantong (CN); Yixiang Lu, Nantong (CN); YunCheng Sun, Nantong (CN); Jinkang Wang, San Francisco, CA (US)

(73) Assignee: Biocross Institute of Molecular Medicine (Nantong) Co., Ltd. (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/388,979

(22) PCT Filed: Sep. 19, 2011

(86) PCT No.: PCT/US2011/052193

§ 371 (c)(1), (2), (4) Date: Apr. 17, 2013

(87) PCT Pub. No.: WO2012/040118

PCT Pub. Date: Mar. 29, 2012

(65) Prior Publication Data

US 2013/0210894 A1 Aug. 15, 2013

(51) Int. Cl.

| | |
|---|---|
| ***A61K 31/70*** | (2006.01) |
| ***C07H 21/02*** | (2006.01) |
| ***C07H 21/04*** | (2006.01) |
| ***C12N 15/113*** | (2010.01) |
| ***A61K 31/713*** | (2006.01) |
| ***C12N 15/115*** | (2010.01) |

(52) U.S. Cl.
CPC ............ *C12N 15/115* (2013.01); *A61K 31/713* (2013.01); *C12N 2310/13* (2013.01); *C12N 2310/16* (2013.01)

(58) Field of Classification Search
None
See application file for complete search history.

(56) References Cited

U.S. PATENT DOCUMENTS 6,397,849 B1 * 6/2002 Bowman .............. A61K 9/0048 128/898
6,818,397 B1 * 11/2004 Lee et al. ...................... 435/6.19
2003/0232074 A1 12/2003 Lipford et al.
2005/0058982 A1 * 3/2005 Han et al. .......................... 435/5
2005/0215501 A1 9/2005 Lipford et al.
2005/0256073 A1 11/2005 Lipford et al.
2006/0172966 A1 8/2006 Lipford et al.
2007/0031844 A1 * 2/2007 Khvorova ............ A61K 31/713 435/6.11
2008/0171716 A1 7/2008 Maclachlan et al.
2008/0317811 A1 12/2008 Andre et al.
2009/0298911 A1 12/2009 Lee et al.

FOREIGN PATENT DOCUMENTS

CN 101857860 A 10/2010

OTHER PUBLICATIONS

Gitlin, et al. (2002) Short Interfering RNA confers intracellular antiviral immunity in human cells, Nature, v.418:430-4.*
U.S. Appl. No. 12/886,446, filed Sep. 20, 2010, Zhu et al.
Akira, et al. Role of adapters in Toll-like receptor signalling. Biochem Soc Trans. Jun. 2003;31(Pt 3):637-42.
Cashman, et al. Inhibition of choroidal neovascularization by adenovirus-mediated delivery of short hairpin RNAs targeting VEGF as a potential therapy for AMD. Invest Ophthalmol Vis Sci. Aug. 2006;47(8):3496-504.
Forsbach, et al. Identification of RNA sequence motifs stimulating sequence-specific TLR8-dependent immune responses. J Immunol. Mar. 15, 2008;180(6):3729-38.
International search report and written opinion dated Jan. 20, 2012 for PCT Application No. US11/52193.
Kleinman, et al. Sequence- and target-independent angiogenesis suppression by siRNA via TLR3. Nature. Apr. 3, 2008;452:591-7.
Maloney, et al. Choroidal neovascular membranes express toll-like receptor 3. Ophthalmic Res. 2010;44(4):237-41.
Mariotti, et al. Polymorphisms within the Toll-Like Receptor (TLR)-2, -4, and -6 Genes in Cattle. Diversity. 2009;1:7-18.
Reich, et al. Small interfering RNA (siRNA) targeting VEGF effectively inhibits ocular neovascularization in a mouse model. Mol Vis. May 30, 2003;9:210-6.
Voest, et al. Inhibition of angiogenesis in vivo by interleukin 12. J Natl Cancer Inst. Apr. 19, 1995;87(8):581-6.

* cited by examiner

*Primary Examiner* — Jennifer Pitrak McDonald
(74) *Attorney, Agent, or Firm* — Fox Rothschild LLP; Jianming Jimmy Hao

(57) ABSTRACT

This invention relates to the application of the highly conserved sequences of viral genome, especially from a highly conserved domain of enteroviral genome as templates to design target small ligand RNAs (sliRNAs). The resulting sliRNAs are therapeutically active ingredients in the treatment of the related diseases caused by pathological angiogenesis.

17 Claims, 12 Drawing Sheets

Enterovirus [viruses]
. Human enterovirus D [viruses]

| | | | | |
|---|---|---|---|---|
| . . Human enterovirus 70 ---------- | 13329 | 21 hits | [viruses] | Human enterovirus 70 strain J670/71, complete genome |
| . . Human enterovirus 94 .......... | 5530 | 2 hits | [viruses] | Human enterovirus 94 isolate E210, complete genome |
| . . Human enterovirus 68 .......... | 4325 | 2 hits | [viruses] | Human enterovirus 68 strain Fermon, complete genome |
| . Human poliovirus 2 -------------- | 1032 | 11 hits | [viruses] | Human poliovirus 2 RNA for polyprotein, complete genome, ge |
| . Human coxsackievirus A22 ...... | 1014 | 13 hits | [viruses] | Human coxsackievirus A22 strain ban99-10427, complete genome |
| . Human coxsackievirus A1 ........ | 984 | 4 hits | [viruses] | Human coxsackievirus A1 strain Tompkins, complete genome |
| . Human coxsackievirus A19 ...... | 960 | 4 hits | [viruses] | Human coxsackievirus A19 strain 8663, complete genome |
| . Human enterovirus 90 ............ | 958 | 17 hits | [viruses] | Human enterovirus 90 isolate F950027, complete genome |
| . Human coxsackievirus A11 ...... | 917 | 10 hits | [viruses] | Human coxsackievirus A11 strain BAN00-10444, complete genome |
| . Human enterovirus 99 ............ | 906 | 8 hits | [viruses] | Human enterovirus 99 strain USA-Ok85-10627 polyprotein gene |
| . Human poliovirus 1 ............... | 895 | 117 hits | [viruses] | Human poliovirus 1 RUS-1161-96-001, complete genome |
| . Human coxsackievirus A20 ...... | 893 | 15 hits | [viruses] | Human coxsackievirus A20 strain CVA20b-Cecil polyprotein ge |
| . Human coxsackievirus A17 ...... | 886 | 3 hits | [viruses] | Human coxsackievirus A17 strain BAN03-10616, complete genome |
| . Human coxsackievirus A24 ...... | 838 | 4 hits | [viruses] | Human coxsackievirus A24 strain Joseph, complete genome |
| . Human poliovirus 3 ................ | 834 | 8 hits | [viruses] | Human poliovirus type 3 complete genome, live-attenuated st |
| . Human enterovirus 96 ............ | 830 | 4 hits | [viruses] | Human enterovirus 96 isolate FIN04-7, complete genome |
| . Human poliovirus 1 Mahoney .... | 825 | 3 hits | [viruses] | Human poliovirus 1 Mahoney, complete genome |
| . Human coxsackievirus A21 ...... | 814 | 4 hits | [viruses] | Human coxsackievirus A21 strain BAN00-10542 polyprotein gen |
| . Human poliovirus 1 strain Sabin . | 812 | 1 hits | [viruses] | Human poliovirus 1 strain Sabin 1 complete genome, strain Sab |

FIGURE 17b

APPLICATION OF HIGHLY CONSERVED DOMAIN SEQUENCES FROM VIRAL GENOME AS TEMPLATE TO DESIGN THERAPEUTIC SLIRNAS

CROSS-REFERENCE

This application is a U.S. National Phase of International Application No. PCT/US2011/52193, filed Sep. 19, 2011, which claims the benefit of U.S. application Ser. No. 12/886,446, filed Sep. 20, 2010. The disclosures of all applications are incorporated by reference in their entireties.

REFERENCE TO A SEQUENCE LISTING

The instant application contains a Sequence Listing which is been submitted in ASCII format via EFS-Web and is hereby incorporated by reference in its entirety. Said ASCII copy, created on 19 Sep. 2011, is named Doc. No. 4170050_1.txt and is 9.28 KB in size.

BACKGROUND OF THE INVENTION

Small interfering RNA (siRNA) is a short double-stranded RNA fragment with specific gene code. Generally the functional length is 21-23 nucleotides. siRNA specifically binds to complementary mRNA, which leads to the degradation and malfunction of the target. The phenomenon of post-transcriptional gene silencing mediated efficiently by siRNA is called RNAi (RNA interference), which is a defense mechanism naturally present in cells. When a double-stranded RNA enters into the cell, it is excised into siRNA fragments with 21-25 nucleotides. The fragments first bind with the other components in cells to form a nucleic acid-protein complex, which is called the RNA-induced silencing complex (RISC). The activated RISC targets a homologous mRNA by base pairing, resulting in the cleavage and degradation of the mRNA, after which cell-specific gene expression is inhibited. The siRNA is not only widely used in biomedical research, but also in the treatment of various diseases such as viral infection, cancer, vascular diseases, disorders of the nervous system and others.

Age-related macular degeneration (AMD) is one of the leading causes of vision irreversible damage in people over the age of 50 years. AMD is clinically divided into two types as “dry” and “wet”. The wet AMD develops rapidly and often results in blindness. The pathological changes of the disease cause severe visual impairment. The manifestations of AMD include the retinal pigment epithelial cells (RPE) dysfunction and choroidal neovascularization (CNV) in the macular area. Fluid leakage, RPE or neural epithelial detachment and bleeding from ruptured blood vessels can occur in severe cases. It has been found that many cellular factors play important roles in regulation in CNV generation, among which are vascular endothelial growth factor (VEGF), VEGF receptor (VEGFR), hypoxia inducible factor (HIF), angiopoietin (Ang) and other cytokines, mitogen-activated protein kinases (MAPK) and others.

RNAi has been tested for the efficacy of inhibiting CNV, Cashman et al. (Cashman et al. IOVS. 2006; 47: 3496-3504) intravitreally injected the VEGF short hairpin RNA (shRNA) constructed in adenoviral expression vectors into mice CNV model which was induced by VEGF165. The treatment effectively inhibits the over-expression of VEGF and successfully prevented the formation of CNV. The evidences showed that the shRNA adenoviral vector was delivered (transmembrane) into the cytoplasm and triggered the activation of RISC, accompanied the degradation of the target mRNA. Due to the concern of the clinical application for adenoviral vector, an attempt was made to use the naked (no transmission medium) VEGF siRNA to silence the target gene. The results indicated that inhibition of the VEGF expression via the naked “siRNA” did reduce the formation of CNV in a mice model (Reich et al. Mol. Vis. 2003; 9: 210-216).

There is still a need for improved RNA based inhibitors for the treatment of diseases such as AMD and CNV.

SUMMARY OF THE INVENTION

In one aspect, the present invention provides an sliRNA for modulating a Toll-like Receptor (TLR), comprising a nucleotide sequence that is at least 80% identical to a fragment of a highly conserved domain of a viral genome sequence. In some embodiments, the nucleotide sequence is at least 85%, 90%, 95%, or 100% identical to the fragment of the highly conserved domain. In some embodiments, the Toll-like Receptor is Toll-like Receptor 3 (TLR3). In some embodiments, the highly conserved domain is located in a region of the virus genome selected from the group consisting of: 5 ‘un-translation region (UTR), 3’ UTR, and open reading frame (ORF). In some embodiments, the virus is a human virus selected from the group consisting of: poliovirus, coxsackievirus, echovirus, picornavirus, and enterovirus. In some embodiments, the highly conserved domain sequence is located in nucleotides from 241 to 263 of SEQ ID NO: 1. In some embodiments, the sliRNA comprises a double stranded RNA, which can be blunt ended or have 3' or 5' overhang. In some embodiments, the sliRNA has a length of 14 to 25 nucleotides. In some embodiments, the sliRNA comprises 1 to 2 bases of DNA at the 3'-end of the nucleotide sequence.

In another aspect, the present invention provides an sliRNA comprising a double-stranded RNA molecule having the following sequences:

```
Sense:
                                    (SEQ ID NO: 14)
5'-UAGGUACUUCGAGAAGCCUAGUANn-3'

Antisense:
                                    (SEQ ID NO: 15)
5'-UACUAGGCUUCUCGAAGUACCUANn-3',
or:

Sense:
                                    (SEQ ID NO: 28)
5'-AGGUACUUCGAGAAGCCNn-3'

Antisense:
                                    (SEQ ID NO: 29)
5'-GGCUUCUCGAAGUACCUNn-3'
```

wherein N is a nucleotide selected from the group consisting of: cytosine, guanine, adenine, and thymine, and the deoxygen forms thereof, and wherein n is an integer from 0 to 2. In some embodiments, the N is dT and n is 2. In some embodiments, n is 2.

In yet another aspect, the present invention provides a pharmaceutical composition, comprising the sliRNA provided herein, and a pharmaceutical acceptable carrier.

In another aspect, the present invention provided a method for treating a pathological angiogenesis related disease, comprising administering a pharmaceutically effective amount of the sliRNA provided herein to a subject in need of such treatment. In some embodiments, the disease is selected from the group consisting of: age-related macular degeneration (AMD), diabetic retinopathy, and cancer.

In another aspect, the present invention provides a method for designing an sliRNA, comprising: selecting a highly conserved domain of a viral genome sequence; and testing a RNA comprising a nucleotide sequence that is at least 80%, 85%, 90%, 95%, or 100% identical to a fragment of a highly conserved domain for the ability of the RNA to modulate the activity of a TLR, such as TLR3.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which.

FIGS. 17*a* and 17*b* shows the highly conserved domain of the virus genome.

DETAILED DESCRIPTION OF THE INVENTION

Figure 1:
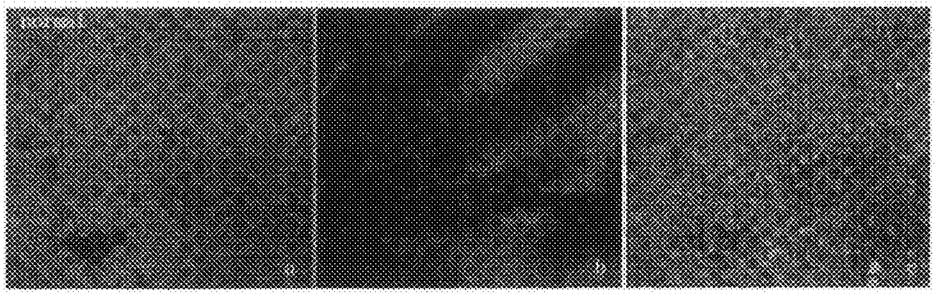
FIG. 1 depicts the fluorescence micrographs of sclera-choroid/retinal pigment epithelium (RPE) flatmount (magnification 40×): A green channel image shows phalloidin-positive RPE cells in uniform hexagonal close arrangements (FIG. 1*a*); a red channel image shows isolectin-$B_4$(iB4)-positive vessel endothelial cells (FIG. 1*b*); an merged image of green-red-blue channels shows the overlay of RPE, vessel endothelial cells and nuclei labeled by 4',6'-diamidino-2-phenylindole (DAPI) (FIG. 1*c*).

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

The terminology used herein is for the purpose of describing particular embodiments only and is not intended to be limiting of the invention. As used herein, the singular forms “a”, “an” and “the” are intended to include the plural forms as well, unless the context clearly indicates otherwise. Furthermore, to the extent that the terms “including”, “includes”, “having”, “has”, “with”, or variants thereof are used in either the detailed description and/or the claims, such terms are intended to be inclusive in a manner similar to the term “comprising”.

The term “about” or “approximately” means within an acceptable error range for the particular value as determined by one of ordinary skill in the art, which will depend in part on how the value is measured or determined, i.e., the limitations of the measurement system. For example, “about” can mean within 1 or more than 1 standard deviation, per the practice in the art. Alternatively, “about” can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term “about” meaning within an acceptable error range for the particular value should be assumed.

I. Small Ligand RNAs

In one aspect, the present invention provides compositions and methods related to an sliRNA for modulating a Toll-like Receptor (TLR), the RNA comprises a nucleotide sequence that is at least 80% identical to a fragment of a highly conserved domain of a viral genome sequence.

By small ligand RNA (“sliRNA”) herein is meant a RNA that acts as a ligand for a TLR.

By “modulation” or “modulation of expression” herein is meant either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

Toll-Like Receptors

Toll-like Receptors (TLRs) play an important role in the recognition of components of pathogens and subsequent activation of the innate immune response, which then leads to development of adaptive immune responses. The TLRs consist of a large extracellular domain responsible for pathogen associated molecular pattern (PAMP) binding, a transmembrane domain and an intracellular Toll/interleukin-1 receptor (TIR) domain which binds molecules and initiates cellular immune responses. There are at least 10 members of TLRs specifically to recognize molecular patterns from all major classes of pathogens have been identified in mammals, eleven in mice. TLRs operate with diverse variety of ligands ranging from hydrophilic nucleic acid to LPS; furthermore, the heterodimerization expands the ligand spectrum. TLR2 and TLR4 recognize bacterial cell components. TLR6 in association with TLR2 recognizes a wide variety of bacterial cell wall components (Mariotti et al. Diversity 2009, 1, 7-18).

In some embodiments, the Toll-like Receptor is Toll-like Receptor 3 (TLR3).

TLR3 recognizes double-stranded (ds) RNA. Viral replication within infected cells results in the generation of dsRNA, suggesting that its extracellular domain responsible for dsRNA binding (Akira et al. Biochem Soc Trans. 2003; 31: 637-642). A proposed mechanism for the observed anti-angiogenic function of TLR3 is via activation of IL12 and IFN-'y, 2 mediators that have been shown to inhibit neovascularization (Voest et al. J Natl Cancer Inst 1995; 87: 581-586.19).

The RISC-mediated gene silencing requires the delivery of siRNA into the cytoplasm. However, the naked "siRNA" is unable to penetrate through the biomembrane. The mystery of the CNV inhibition by naked "siRNA" remained unknown until a recent report by Dr. Kleinman et al. (Kleinman et al. Nature, 2008; 452: 591-597). They found that the naked "siRNA"-based CNV suppression was achieved by activating cell surface toll-like receptor 3 (TLR3) rather than by RISC and the suppression was RNA sequence-independent. More recently, another group confirmed that "siRNA"-mediated signaling through TLR3 enabled to suppress experimentally induced CNV independent of the gene targeted by the "siRNA" (Maloney et al. Ophthalmic Res 2010; 44: 237-241).

Chemical Composition of sliRNAs

The sliRNA of the present invention comprises single-stranded or double-stranded oligonucleotides.

The term "double-stranded RNA" or "dsRNA", as used herein, refers to a ribonucleic acid molecule, or complex of ribonucleic acid molecules, having a duplex structure including two anti-parallel and substantially complementary, as defined herein, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5'end of the respective other strand forming the duplex structure, the connecting structure is referred to as a "linker." The RNA strands may have the same or a different number of nucleotides. The maximum number of base pairs is the number of nucleotides in the shortest strand of the dsRNA. In addition to the duplex structure, a dsRNA may comprise one or more nucleotide overhangs. A dsRNA as used herein is also referred to as a "small ligand RNA" or "sliRNA".

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to the corresponding segment of a highly conserved domain sequence of a viral genome sequence. As used herein, the term "region of complementarity" refers to the region on the antisense strand that is substantially complementary to a sequence, for example a target sequence, as defined herein. Where the region of complementarity is not fully complementary to a highly conserved domain sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand. Sense strand generally is the same strand as a RNA transcribed from a viral genome, preferably an RNA encoding a protein.

The term "identity" is the relationship between two or more polynucleotide sequences, as determined by comparing the sequences. Identity also means the degree of sequence relatedness between polynucleotide sequences, as determined by the match between strings of such sequences. While there exist a number of methods to measure identity between two polynucleotide sequences, the term is well known to skilled artisans (see, e.g., Sequence Analysis in Molecular Biology, von Heinje, G., Academic Press (1987); and Sequence Analysis Primer, Gribskov., M. and Devereux, J., eds., M. Stockton Press, New York (1991)). "Substantially identical," as used herein, means there is a very high degree of homology (e.g., 100% sequence identity) between the sense strand of the dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is typical, the dsRNA may contain single or multiple base-pair random mismatches between the RNA and the highly conserved domain sequence.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. In some embodiments, the presence of only one nucleotide overhang strengthens the activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, i.e., less than 5 mg/kg body weight of the recipient per day. In one embodiment, the antisense strand of the dsRNA has 1-10 nucleotides overhangs each at the 3' end and the 5' end over the sense strand. In one embodiment, the sense strand of the dsRNA has 1-10 nucleotides overhangs each at the 3' end and the 5' end over the antisense strand. In another embodiment, one or more of the nucleotides in the overhang is replaced with a nucleoside thiophosphate.

In some embodiments, the sliRNA comprises RNA: RNA duplex with 0, 1, 2, 3, 4, or 5 base pairs of DNA attached to the 3' end or 5' end of the RNA: RNA duplex. In some embodiments, attachment of the DNA base pairs to the 3'end is preferred. The base pairs can have 1, 2, 3, or 4 nucleotides overhang. In some embodiments, a blunt end DNA base pair is preferred. In some embodiments, the DNA is preferably a T, or dT.

In some embodiments, the sliRNA comprises 1, 2, 3, 4, or 5 bases of deoxyribonucleotides at the 3'-end of the nucleotide sequence. The bases can be cytosine (C), guanine (G), adenine (A), uracil (U), deoxycytidine (dC), deoxyguanosine (dG), deoxyadenine (dA), or deoxythymidine (dT), or analogues thereof.

In the context of this invention, the term "oligonucleotide" refers to an oligomer or polymer of ribonucleic acid (RNA) or deoxyribonucleic acid (DNA) or mimetics thereof.

As used herein, the term "oligonucleotide", includes linear or circular oligomers of natural and/or modified monomers or linkages, including deoxyribonucleosides, ribonucleosides, substituted and alpha-anomeric forms thereof, peptide nucleic acids (PNA), linked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoogsteen or reverse Hoogsteen types of base pairing, or the like.

The oligonucleotide may be "chimeric", that is, composed of different regions. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in In some embodiments, the region of the oligonucleotide which is modified comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrymidines, abasic residues or an inverted base at the 3' end of the RNA. The effect of such increased affinity is to greatly enhance sliRNA oligonucleotide inhibition of gene expression. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance.

Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. *Acc. Chem. Res.* 1995, 28:366-374.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc (ref: Recent advances in the medical chemistry of antisense oligonucleotide by Uhlman, Current Opinions in Drug Discovery & Development 2000 Vol 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, most preferably less than about 50% LNA monomers and that their sizes are between about 10 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in o Nielsen et al., *Science,* 1991, 254, 1497-1500.

In a more preferred embodiment of the invention the oligonucleotides with phosphorothioate backbones and oligonucleosides with heteroatom backbones, and in particular $—CH_2—NH—O—CH_2—$, $—CH_2—N(CH_3)—O—CH_2—$ known as a methylene (methylimino) or MMI backbone, $—CH_2—O—N(CH_3)—CH_2—$, $—CH_2N(CH_3)—N(CH_3)CH_2—$ and $—O—N(CH_3)—CH_2—CH_2—$ wherein the native phosphodiester backbone is represented as —O—P—O—$CH_2$— of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O-, S- or N-alkynyl; or O-alkyl-O-alkyl, wherein the alkyl, alkenyl and alkynyl may be substituted or unsubstituted C to CO alkyl or $C_2$ to CO alkenyl and alkynyl. Particularly preferred are $O[(CH_2)_nO]_nCH_3$, $O(CH_2)_nOCH_3$, $O(CH_2)_nNH_2$, $O(CH_2)_nCH_3$, $O(CH_2)_nONH_2$, and $O(CH_{2n}ON[(CH_2)_nCH_3)]_2$ where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further preferred modification comprises 2'-dimethylaminooxyethoxy, i.e., a $0(CH_2)_2ON(CH_3)_2$ group, also known as 2'-DMA0E, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N $(CH_2)_2$, also described in examples herein below.

Other preferred modifications comprise 2'-methoxy (2'-O $CH_3$), 2'-aminopropoxy (2'-O $CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Oligonucleotides may also comprise nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopaedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications.

Representative United States patents that teach the preparation of the above noted modified nucleobases as well as other modified nucleobases comprise, but are not limited to, U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N. Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Mancharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., *J. Pharmacol. Exp. Ther.,* 1996, 277, 923-937).

Representative United States patents that teach the preparation of such oligonucleotide conjugates comprise, but are not limited to, U.S. Pat. Nos. 4,828,979; 4,948,882; 5,218, 105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Sequence of sliRNAs

In some embodiments, the nucleotide sequence is at least 85%, 86%, 87%, 88%, 89%, 90%, 91%, 92%, 93%, 94%, 95%, 96%, 97%, 98%, 99%, or 100% identical to a fragment of a highly conserved domain of a viral genome as provided herein.

In some embodiments, the highly conserved domain sequence is located in nucleotides from 241 to 263 of SEQ ID NO: 1.

II. Method of Designing Small Ligand RNAs

In another aspect, the present invention provides a method for designing an sliRNA, comprising: selecting a highly conserved domain of a viral genome sequence; and testing an RNA comprising a nucleotide sequence that is at least 80%, 85%, 86%, 87%, 88%, 89%, 90%, 91%, 92%, 93%, 94%, 95%, 96%, 97%, 98%, 99% identical to a fragment of the highly conserved domain for the ability of the RNA to modulate the activity of a Toll-like Receptor (TLR), such as Toll-like Receptor 3 (TLR3).

The virus sequence that can be used in the present invention can be of any viruses known in the art. Suitable viruses include, but are not limited to: single-stranded RNA (ssRNA) viruses, double-stranded (dsRNA) RNA viruses.

In some embodiments, the virus is an dsRNA virus, include, but are not limited to Infectious pancreatic necrosis virus, Infectious bursal disease virus, Helminthosporium victoriae virus, Cystovirus, Hypovirus, Partitivirus, Alphacryptoviruses, Betacryptoviruses, Rotavirus, and etc.

In some embodiments, the virus is an ssRNA virus, include, but are not limited to Coronavirus, SARS, Okavirus, Himetobi P virus, Plautia stali intestine virus, Rhopalosiphum padi virus, Homalodisca coagulata virus 1 (HoCV-1), Acheta domesticus virus, Marnavirus, Enterovirus, rhinovirus, Poliovirus, the common cold virus, Hepatitis A virus, Encephalomyocarditis virus, Parechovirus, Equine rhinitis B virus, Seneca Valley virus, poliovirus, Cheravirus, Sadwavirus, Sequivirus, Torradovirus, Waikavirus, Nepovirus, Black raspberry necrosis virus, Norwalk virus, Yellow fever virus, West Nile virus, Hepatitis C virus, Dengue fever virus, Betatetravirus, Omegatetravirus, Rubella virus, Ross River virus, Sindbis virus, Chikungunya virus, Hepatitis E virus, Herpesvirus, Ebola virus, Marburg virus, Measles virus, Mumps virus, Nipah virus, Hendra virus, Rabies virus, Ippy virus, Lassa virus, Lujo virus, Lymphocytic choriomeningitis virus, Mobala virus, Mopeia virus, Amapari virus, Chapare virus, Flexal virus, Guanarito virus, Junin virus, Latino virus, Machupo virus, Oliveros virus, Parana virus, Pichinde virus, Pirital virus, Sabiá virus, Tacaribe virus, Tamiami virus, Whitewater Arroyo virus, Hantaan virus, Dugbe virus, Bunyamwera virus, Rift Valley fever virus, Influenzavirus, Isavirus and Thogotovirus, Hepatitis D virus, Hepatitis B virus, and etc.

After the virus is selected, the genome sequences of different species and/strains of the virus are obtained from various databases (e.g., GenBank), or by de novo sequencing. Preferably, the different species and/strains of the virus are from human or primates closely related to human, such as monkey, lemur, chimpanzee, and the like.

The genome sequences of different species and/strains of the virus are then aligned using software known in the art (e.g. GCG package) to identify highly conserved domain. By "highly conserved domain" herein is meant a domain, or a stretch of sequence that are conserved among the different species and/strains of the virus. Preferably, the domain is an identity from 75% to 100%, and preferably from 90 to 100%.

After the highly conserved domain is determined, the sequence of a fragment of the highly conserved domain is then used to design the sliRNA of the invention.

In some embodiments, the highly conserved domain is located in a region of the virus genome selected from the group consisting of: 5 'un-translation region (UTR), 3' UTR, and open reading frame (ORF).

The sliRNAs have the structure, sequence and chemical composition (e.g. modifications) as described herein.

In some embodiments, the sliRNA is from about 14 to about 25 bp long, preferably from about 17 to about 23 bps long (e.g., 17, 18, 19, 20, 21, 22, 23, 24, 25), and preferably has a GC content of about 30-60%, more preferably about 35%, 40%, 45%, 50%, or 55%.

Preferably, the sliRNA has no homology to human genes, especially human functional gene. In general, the sliRNA has no, or less than 50%, 55%, 60%, 65%, 70%, 75%, 80%, 85%, 95%, or 95% identity to a human gene.

In some embodiments, the sliRNA comprises a double-stranded RNA, which can be blunt ended or have 3' or 5' overhang. In some embodiments, the sliRNA has a length of 14 to 25 nucleotides.

In some embodiments, the sliRNA has 1, 2, 3, 4, or 5 DNA bases attached to the 5' and/or 3' end of the RNA:RNA duplex. In some embodiments, the DNA base is attached to the 3' end, and preferably forms a blunt end.

The sliRNA designed then are synthesized by the methods provided herein or known in the art.

The synthesized sliRNA are tested for its ability to modulate TLR (e.g., TLR3) in in vitro assays, in vivo assays, or animal models provided herein or known in the art.

In some embodiments, the ability for the sliRNA to modulate TLR3 is assayed by measuring the expression level (mRNA and/or protein) of TLR3, IL-12, NF-κB, or other biomarkers.

In some embodiments, the sliRNA is tested in a rat aortic ring assay or a NF-κB activity assay as provided herein.

In some embodiments, the sliRNA is tested in an Mice CNV Model as provided herein.

In general, a batch of sliRNAs is designed and synthesized, preferably includes all the possible sliRNAs for a given virus genome. In some embodiments, a series of sliRNA are designed with one or more bases overlap to cover the entire highly conserved domain of a viral genome.

After one or more lead sliRNAs are identified, they can be further optimized by adjusting sequence, structure, modification, etc., to achieve desired characteristics, such as DM and PK.

Characteristics of sliRNA include, but are not limited to, stability, efficacy, and toxicity.

The sliRNA may also be optimized in conjunction with a delivery system as provided herein, or known in the art.

III. Method of Treatments

In another aspect, the present invention provided a method for treating a pathological angiogenesis related disease, comprising administering a pharmaceutically effective amount of the sliRNA provided herein to a subject in need of such treatment. In some embodiments, the disease is selected from the group consisting of: ocular neovascularization diseases such as Diabetic Retinopathy (DR), Age related macular degeneration (AMD), Uveitis, Stromal Keratitis (SK) and cancers.

The term "subject," or "individual" as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the mammal is a human.

IV. Pharmaceutical Compositions and Delivery

In yet another aspect, the present invention provides a pharmaceutical composition, comprising the sliRNA of provided herein, and a pharmaceutical acceptable carrier.

The present invention provides the preparation of sliRNA molecules to treat pathological angiogenesis-related diseases. The associated formulations of drugs vary in compliance with the administration of the corresponding diseases and are appropriate to maintain the activity of sliRNA molecules. For example, for injectable drug together with proper delivery systems, the formulation can be a lyophilized powder.

Optionally, the above drug formulations can contain any pharmaceutical acceptable adjuvant, as long as the appropriate delivery systems suitable and appropriate to maintain the activity of sliRNA molecules.

For example, in clinical application of ophthalmic drugs, the sliRNA of the present invention can be dissolved in sterile water free of RNA enzymes. The sliRNA concentration is adjusted to 1 μg/μL. The intravitreal injection is performed after gentle mixture of the preparation. The injection is conducted once every two weeks, 4 weeks as a course of a treatment.

In another preferred embodiment, treatment of a patient comprises administration one or more of the RNA compounds, in conjunction with other therapies, for example, chemotherapy, radiation, surgery, anti-inflammatory agents and the like. The other agents can be administered, prior to, after or co-administered with the RNA compounds.

The RNA compounds of the invention encompass any pharmaceutically acceptable salts, esters, or salts of such esters, or any other compound which, upon administration to an animal comprising a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bio-equivalents.

The term "prodrug" indicates a therapeutic agent that is prepared in an inactive form that is converted to an active form (i.e., drug) within the body or cells thereof by the action of endogenous enzymes or other chemicals and/or conditions.

The term "pharmaceutically acceptable salt" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Metals used as cations comprise sodium, potassium, magnesium, calcium, and the like. Amines comprise N—N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. Pharma Sci.,* 1977, 66, 119). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

As used herein, a "pharmaceutical addition salt" comprises a pharmaceutically acceptable salt of an acid form of one of the components of the compositions of the invention. These comprise organic or inorganic acid salts of the amines. Preferred acid salts are the hydrochlorides, acetates, salicylates, nitrates and phosphates. Other suitable pharmaceutically acceptable salts are well known to those skilled in the art and comprise basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in Nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and comprise alkaline, alkaline earth, ammonium and quaternary ammonium cations. Carbonates or hydrogen carbonates are also possible. For oligonucleotides, preferred examples of pharmaceutically acceptable salts comprise but are not limited to: (I) salts formed with cations such as sodium, potassium, ammonium, magnesium, calcium, polyamides such as spermine and spermidine, and the like; (II) acid addition salts formed with inorganic acids, for example hydrochloric acid, hydrobromic acid, sulfuric acid, phosphoric acid, nitric acid and the like; (III) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, napthalenesulfonic acid, methanesulfonic acid, p-toluenesulfonic acid, naphthalenedisulfonic acid, polygalacturonic acid, and the like; and (IV) salts formed from elemental anions such as chlorine, bromine, and iodine.

The RNA compounds of the present invention can be utilized for diagnostics, therapeutics, prophylaxis and as research reagents and kits. For therapeutics, an animal, preferably a human, suspected of having a disease or disorder, which can be treated by modulating the expression of a target gene is treated by administering RNA compounds in accordance with this invention. The compounds of the invention can be utilized in pharmaceutical compositions by adding an effective amount of an sliRNA compound to a suitable pharmaceutically acceptable diluent or carrier. Use of the RNA compounds and methods of the invention may also be useful prophylactically.

The present invention also comprises pharmaceutical compositions and formulations, which comprise the RNA compounds of the invention. The pharmaceutical compositions of the present invention may be administered in a number of ways depending upon whether local or systemic treatment is desired and upon the area to be treated. Administration may be topical (comprising ophthalmic and to mucous membranes comprising vaginal and rectal delivery), pulmonary, e.g., by inhalation of powders or aerosols, comprising by nebulizer, intratracheal, intranasal, epidermal and transdermal), oral or parenteral.

Pharmaceutical compositions of the present invention comprise, but are not limited to, solutions, emulsions, and liposome-containing formulations. These compositions may be generated from a variety of components that comprise, but are not limited to, preformed liquids, self-emulsifying solids and self-emulsifying semisolids.

Pharmaceutical compositions of the present invention comprise sliRNA in the amount of 0.5 mg-3 mg per eye.

Pharmaceutical compositions of the present invention are administered once a month (approximately 28 days).

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The co-administration of a nucleic acid and a carrier compound, typically with an excess of the latter substance, can result in a substantial reduction of the amount of nucleic acid recovered in the liver, kidney or other extra circulatory reservoirs, presumably due to competition between the carrier compound and the nucleic acid for a common receptor. For example, the recovery of a partially phosphorothioate oligonucleotide in hepatic tissue can be reduced when it is co-administered with polyinosinic acid, dextran sulphate, polycytidic acid or 4-acetamido-4'isothiocyano-stilbene-2,2'disulfonic acid (Miyao et al., *Antisense Res. Dev.,* 1995, 5, 115-121; Takakura et al., *Antisense & Nucl. Acid Drug Dev.,* 1996, 6, 177-183).

Certain embodiments of the invention provide pharmaceutical compositions containing one or more RNA compounds and one or more other chemotherapeutic agents which function by a non-TRL related mechanism.

Examples of such chemotherapeutic agents comprise, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MIX), colchicine, vincristine, vinblastine, etoposide, teniposide, cisplatin and diethylstilbestrol (DES). See, generally, The Merck Manual of Diagnosis and Therapy, 15th Ed., Berkow et al., eds., 1987, Rahway, N.J., pages 1206-1228).

Anti-inflammatory drugs, comprising but not limited to nonsteroidal anti-inflammatory drugs and corticosteroids, and antiviral drugs, comprising but not limited to ribivirin, vidarabine, acyclovir and ganciclovir, may also be combined in compositions of the invention (The Merck Manual of Diagnosis and Therapy, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

In another related embodiment, compositions of the invention may contain one or more RNA compounds, particularly sliRNAs with different sequences. Two or more combined compounds may be used together or sequentially.

Nucleic Acid Delivery System

Preferred invention practice involves administering at least one of the foregoing RNA oligonucleotides with a suitable nucleic acid delivery system, e.g. as disclosed in US Pat. Appl. Pub. No. 20090247604, the disclosure of which are incorporated by reference in its entirety.

In one embodiment, that system includes a non-viral vector operably linked to the polynucleotide. Examples of such non-viral vectors include the oligonucleotide alone or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., *J. Neurochem,* 64: 487 (1995); Lim, F., et al., in DNA Cloning: Mammalian Systems, D. Glover, Ed. (Oxford Univ. Press, Oxford England) (1995); Geller, A. I. et al., *Proc Natl. Acad. Sci.: U.S.A.:* 90 7603 (1993); Geller, A. I., et al., Proc Natl. Acad. Sci USA: 87:1149 (1990)], Adenovirus Vectors [LeGal LaSalle et al., *Science,* 259:988 (1993); Davidson, et al., *Nat. Genet.* 3: 219 (1993); Yang, et al., *J. Virol.* 69: 2004 (1995)] and Adeno-associated Virus Vectors [Kaplitt, M. G., et al., *Nat. Genet.* 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors may be an indication for some invention embodiments. The adenovirus vector results in a shorter term expression (e.g., less than about a month) than adeno-associated virus, in some embodiments, may exhibit much longer expression. The particular vector chosen will depend upon the target cell and the condition being treated.

The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum Gene Ther* 4:151 (1993)) and MMT promoters may also be used. Certain proteins can be expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication. See, Sambrook, et al., Molecular Cloning: A Laboratory Manual, Cold Spring Harbor Laboratory press, (1989). Promoters are discussed infra. The plasmid vector may also include a selectable marker such as the β-lactamase gene for ampicillin resistance, provided that the marker polypeptide does not adversely effect the metabolism of the organism being treated. The cassette can also be bound to a nucleic acid binding moiety in a synthetic delivery system, such as the system disclosed in WO 95/22618.

If desired, the polynucleotides of the invention may also be used with a microdelivery vehicle such as cationic liposomes and adenoviral vectors. For a review of the procedures for liposome preparation, targeting and delivery of contents, see Mannino and Gould-Fogerite, *BioTechniques,* 6:682 (1988). See also, Feigner and Holm, *Bethesda Res. Lab. Focus,* 11(2): 21 (1989) and Maurer, R. A., *Bethesda Res. Lab. Focus,* 11(2):25 (1989).

Replication-defective recombinant adenoviral vectors can be produced in accordance with known techniques. See, Quantin, et al., *Proc. Natl. Acad. Sci. USA,* 89:2581-2584 (1992); Stratford-Perricadet, et al., *J. Clin. Invest.,* 90:626-630 (1992); and Rosenfeld, et al., *Cell,* 68:143-155 (1992).

Another preferred antisense oligonucleotide delivery method is to use single stranded DNA producing vectors which can produce the antisense oligonucleotides intracellularly. See for example, Chen et al, *BioTechniques,* 34: 167-171 (2003), which is incorporated herein, by reference, in its entirety.

The effective dose of the nucleic acid will be a function of the particular expressed protein, the particular cardiac arrhythmia to be targeted, the patient and his or her clinical condition, weight, age, sex, etc.

One preferred delivery system is a recombinant viral vector that incorporates one or more of the polynucleotides therein, preferably about one polynucleotide. Preferably, the viral vector used in the invention methods has a pfu (plague forming units) of from about $10^8$ to about $5\times10^{10}$ pfu. In embodiments in which the polynucleotide is to be administered with a non-viral vector, use of between from about 0.1 nanograms to about 4000 micrograms will often be useful e.g., about 1 nanogram to about 100 micrograms.

Embodiments of the invention also relates to expression vector constructs for the expression of the RNA oligonucleotides which contain hybrid promoter gene sequences and possess a strong constitutive promoter activity or a promoter activity which can be induced in the desired case.

Throughout this application, the term "expression construct" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for polymerases. Much of the thinking about how promoters are organized derives from analyses of several viral promoters, including those for the HSV thymidine kinase (tk) and SV40 early transcription units. Promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 b.p. upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 b.p. apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, fl-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constitutively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic Virus, HSV-TK, and avian sarcoma virus.

In a preferred embodiment, tissue specific promoters are used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate.

IRES: In certain embodiments of the invention, the use of internal ribosome entry site (IRES) elements is contemplated to create multigene, or polycistronic, messages. IRES elements are able to bypass the ribosome scanning model of 5' methylated Cap dependent translation and begin translation at internal sites. IRES elements from two members of the picornavirus family (poliovirus and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

Kits

In another aspect, the present invention provides a kit comprises one or more RNA oligonucleotides provided herein. These oligonucleotides can comprise one or more modified nucleobases, shorter or longer fragments, modified bonds and the like. In yet another aspect, the invention provides kits for targeting nucleic acid sequences of cells and molecules associated with modulation of the immune response in the treatment of diseases such as, for example, infectious disease organisms, AMD, angiogenesis related diseases, cancer, autoimmune diseases and the like.

In one embodiment, a kit comprises: (a) an RNA provided herein, and (b) instructions to administer to cells or an individual a therapeutically effective amount of RNA oligonucleotide. In some embodiments, the kit may comprise pharmaceutically acceptable salts or solutions for administering the RNA oligonucleotide. Optionally, the kit can further comprise instructions for suitable operational parameters in the form of a label or a separate insert. For example, the kit may have standard instructions informing a physician or laboratory technician to prepare a dose of RNA oligonucleotide.

Optionally, the kit may further comprise a standard or control information so that a patient sample can be compared with the control information standard to determine if the test amount of RNA oligonucleotide is a therapeutic amount consistent with for example, a shrinking of a tumor.

Embodiments of the invention may be practiced without the theoretical aspects presented. Moreover, the theoretical aspects are presented with the understanding that Applicants do not seek to be bound by the theory presented.

EXAMPLES

It should be understood that the following examples used only to clarify the present invention, but not to limit this invention.

It must be explained, if not specified, that the percentage of following examples are all weight percent content wt %.

Example 1

In order to develop sliRNA based eye medicine which can inhibit CNV via activation of TLR3, we chose enterovirus to be the template for sliRNA design. Enterovirus is a group of ssRNA viruses with only 20-30 nm in diameter. There are 67 species in the group based on the serum classification. We selected the highly conserved 5'untranslated region (5'UTR) of the virus as template to design target RNA. We also chose highly variable sequence of the ORF and 3'UTR as templates to design control RNAs. The chemically synthesized small RNAs based on above design were intravitreally injected into the eyes of the mouse CNV model, respectively. The results showed that CNV inhibition efficiency derived from the highly conserved RNA sequences (5'UTR) was significantly higher than those RNAs designed from the high variability region sequences located in ORF and 3'UTR. We also found that in the eye tissue samples, the highly conserved RNA sequences based CNV inhibition dramatically elevated the mRNA levels of TLR3 and its signaling pathway protein—IL12 (interleukin 12) and down-regulated the VEGF mRNA levels as compared with the both control RNA groups.

These data indicates that the highly conserved domain sequences in viral genome can be used as template to design TLR3 RNA ligand (small ligand RNA, sliRNA). Through efficient and sequence-dependent activation of TLR3 pathway, the sliRNA is of potential to treat CNV of AMD and other pathological angiogenesis-related diseases such as diabetic retinopathy, cancer and etc.

We first found that the RNA target-template-sequence as an efficient ligand to activate TLR3 is located in highly conserved 5'UTR regions in enterovirus, a group of small RNA virus with 67 species. The sequence (SEQ ID NO: 1) is as follow:

```
                                                      (SEQ ID NO: 1)
  1 ttaaaacagc tctggggttg ttcccacccc agaggcccac gtggcggcta gtactccggt

 61 accccggtac ccttgtacgc ctgttttata ctccctttcc caagtaactt tagaagaaat

121 aaactaatgt tcaacaggag ggggtacaaa ccagtaccac cacgaacaca cacttctgtt

181 tccccggtga agttgcatag actgtaccca cggttgaaag cgatgaatcc gttacccgct

241 taggtacttc gagaagccta gtatcatctt ggaatcttcg atgcgttgcg atcagcactc

301 taccccgagt gtagcttggg tcgatgagtc tggacacccc acaccggcga cggtggtcca

361 ggctgcgttg gcggcctacc catggctagc accatgggac gctagttgtg aacaaggtgc
```

-continued

```
421 gaagagccta ttgagctacc tgagagtcct ccggcccctg aatgcggcta atcccaacca

481 cggagcaaat gctcacaatc cagtgagtgg tttgtcgtaa tgcgcaagtc tgtggcggaa

541 ccgactactt tgggcgtccg tgtttccttt tatttttatt atggctgctt atggtgacaa

601 tctgagattg ttatcatata gctattggat tagccatccg gtga.
```

Figure 17A:
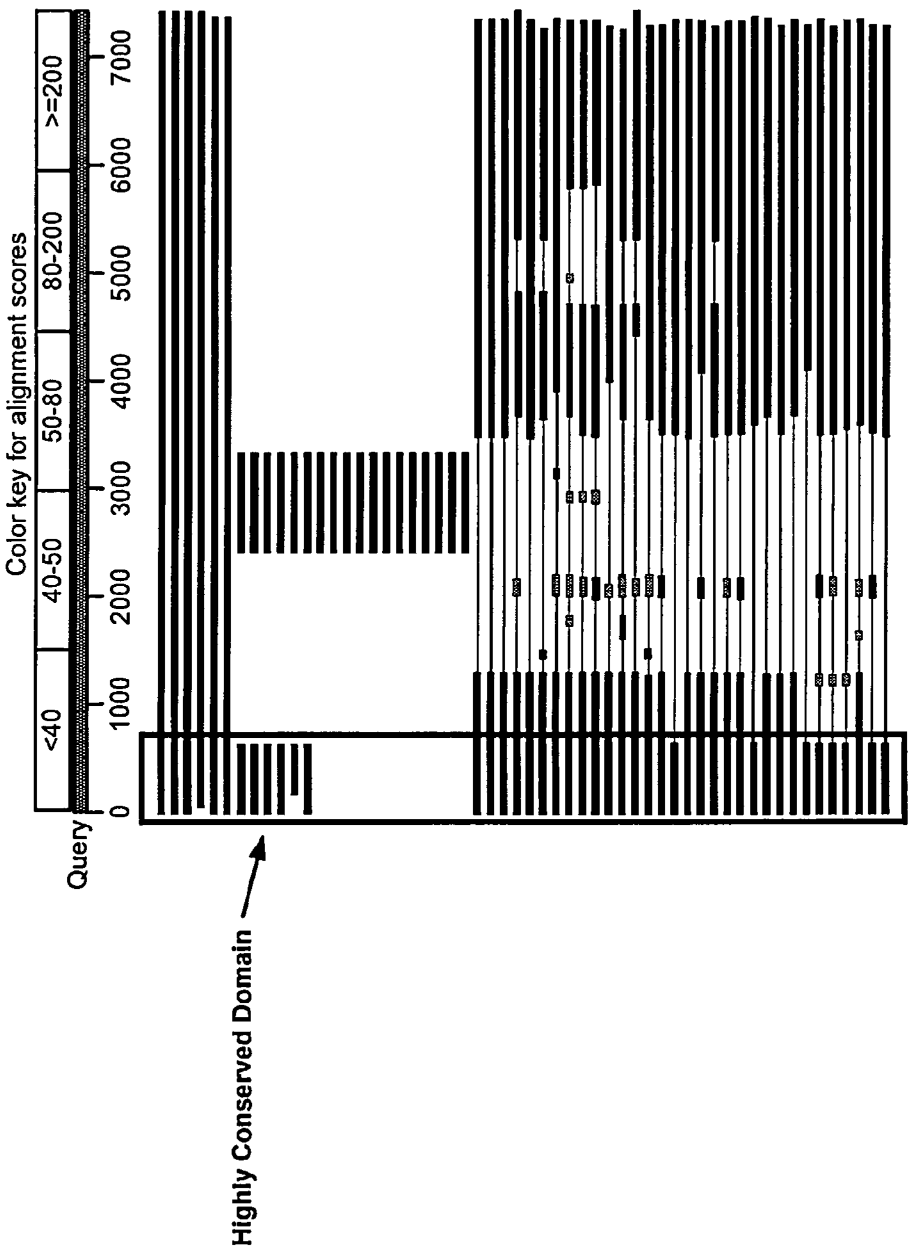

After Blast searching for the RNA viral genomes in NCBI GenBank, we found that the 5'UTR of RNA viral genomes was highly conserved (FIG. 17*a*). And the 5'UTR highly conserved domain was homology with Poliovirous, Coxsackieviruses, Echoviruses and Enteroviruses 68-71, Picornavirus.

We designed TLR3 activating sliRNAs by using the 5'UTR highly conserved domain as template. The randomly designed sliRNAs were homology with four, two or one kind of virus(es), and the sliRNAs homology with four kind of viruses had no homology with human coding genes.

TABLE 1

The GenBank Blast Searching Results on the Randomly Designed sliRNAs GenBank

| sliRNAs | Virus | Homology | Homology Level |
|---|---|---|---|
| siEv70_1 | Human enterovirus 70 | 100% | 1+ |
| siEv70_2 | Human enterovirus 70 | 100% | 4+ |
| | Human echovirus | 100% | |
| | Human poliovirus | 100% | |
| | Human coxsackievirus | 91% | |
| siEv70_3 | Human coxsackievirus | 100% | 4+ |
| | Human enterovirus 70 | 100% | |
| | Human poliovirus | 100% | |
| | Human rhinovirus | 90% | |
| siEv70_4 | Human enterovirus 70 | 100% | 2+ |
| | Simian picornavirus 17 | 100% | |
| siEv70_5 | Human enterovirus 70 | 100% | 1+ |

Figure 18A:
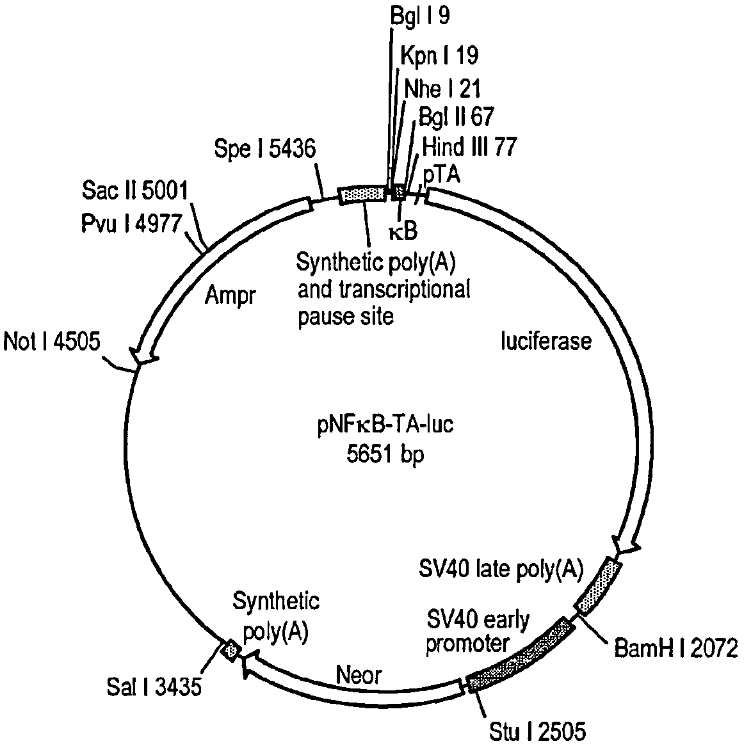
FIG. 18*a* depicts pNF-κB-TA-luc plasmid map.

The siEv70_2 homology with four kinds of virus was selected to experimental validation in vitro Detection of NF-κB Activity in Cell-Based Assay Double stranded viral RNA(dsRNA) is recognized by TLR3. Binding of viral dsRNA to TLR3 initiates the innate immune response by the induction of IL12, IFN-γ. Our objectives in this study were to examine the NF-κB activity induced by siEv70_2 in SMCC-7721 cells, using Poly(I:C) (Invivogen, USA) which was report as TLR3 agonists as a positive control. SMCC-7721 cells were seeded and transfected with pNF-κB-TA-luc plasmid (FIG. 18*a*) by using lipofectamine 2000 (Invitrogen, USA) according to the manufacturer's instructions. pNF-κB-TA-luc plasmid has a NF-κB binding site, which can induced firefly luciferase expression.

fected with pNF-κB-TA-luc and pRL-SV40 (Promega, USA) plasmids (pRL-SV40 as internal control contain renilla luciferase gene). Six hours after transfection, the medium was changed with the medium contain siEv70_2 or Poly(I:C). The NF-κB transcriptional activity was determined using a dual luciferase assay kit (Promega, USA) according to the manufacturer's instructions with ameter (BioTek Synergy HT, USA) after 24 hours.

Figure 18B:
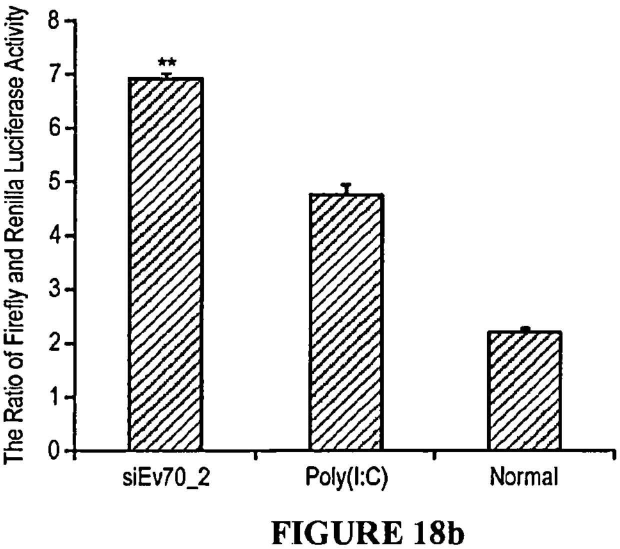
FIG. 18*b* depicts different level of NF-κB activation among different groups.
Figure 19A:
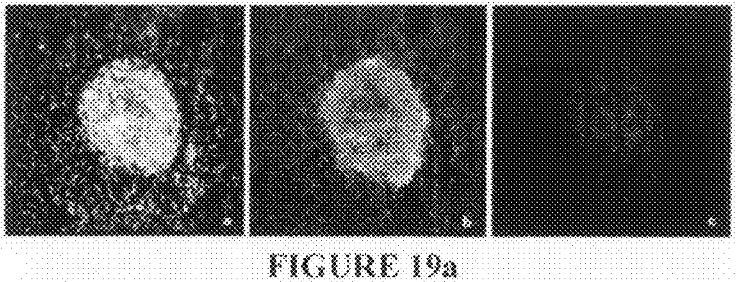
FIG. 19*a* shows the fluorescence micrographs of choroidal flatmount observed under the microscope (magnification 100×). The samples from the day 7 after laser coagulation treated by siEv70_6 were used for comparison. The nucleus, endothelial cells and RPE were labeled by fluorescent DAPI (Blue), isolectin-B4 (Red), and phalloidin (Green) respectively. The CNV inhibition efficiency by siEv70_6 (DNA: RNA hybrid) is less than the dsRNA with the same sequence (siEV70_2).
Figure 19B:
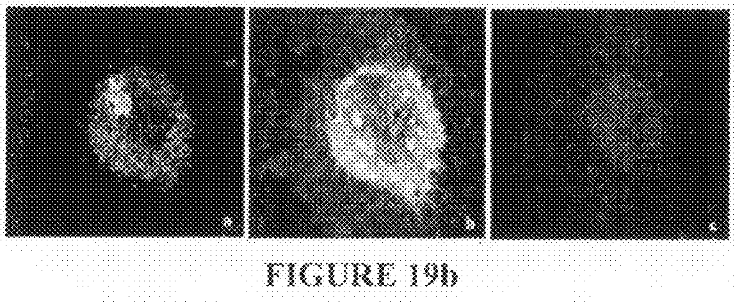
FIG. 19*b* shows the fluorescence micrographs of choroidal flatmount observed under the microscope (magnification 100×). The samples from the day 7 after laser coagulation treatment by siEv70_7 were used for comparison. The nucleus, endothelial cells and RPE were labeled by fluorescent DAPI (Blue), isolectin-B4 (Red), and phalloidin (Green), respectively. There is no obvious effect on CNV inhibition.

Results: According to the value of Firefly luciferase value/Renilla luciferase value, we compared the NF-κB activity induced by siEv70_2 vs. Poly(I:C). Statistically, one-factor analysis of variance between siEv70_2 and Poly(LC) groups showed that the former had much higher NF-κB activity than the later t (P<0.001), indicating that siEv70_2 as TLR3 agonist is stronger than Poly(I:C) (FIG. 18*b*).

Aortic Ring Assay

The rat aortic ring assay for in-vitro study of anti-angiogenesis was done as previously described (Mangiameli et al. J Transl Med 2007; 5: 38). 24 well plates were covered by 150 μL of Matrigel (BD, USA). Thoracic aortas removed from 6- to 8-week-old male Sprague Dawley rats were immediately transferred to a culture dish containing cold serum-free Dulbecco's Modified Eagle Medium (DMEM, Gibco, USA). The periaortic fibroadipose tissue was carefully removed with fine microdissecting forceps and iridectomy scissors paying more attention not to damage the aortic wall. Aortas were sectioned into 1 mm-long cross sections, rinsed several times with endothelial cell medium (ECM). Aortic rings were placed in 24 well plates and covered with an additional 50 μL of Matrigel. The rings were culture in 1 mL of endothelial cell medium for 2 days. Plates were incubated at 37° C., in humidified $CO_2$ and the medium was replaced daily. As microvessels began to branch, some wells with aortic rings were kept as control and other well treated with siEv70_2; avastin and 5% glucose. The plates were cultured with another 4 days. The assay was scored from 0 (least positive) to 5 (most positive) in a double-blinded manner. Each data point was assayed in sextuplets.

Figure 20:
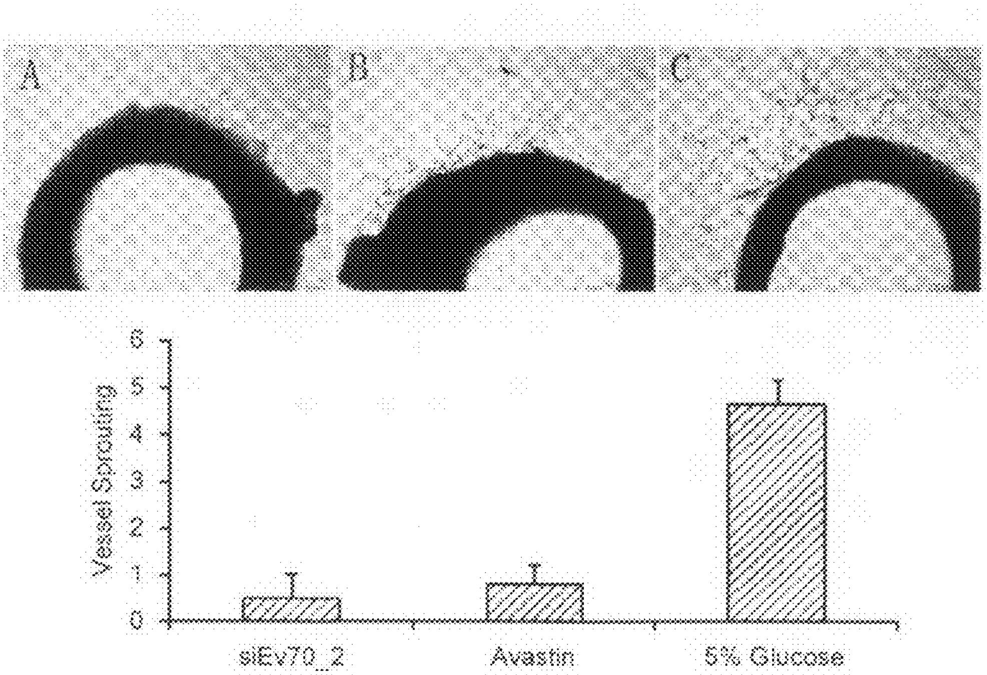
FIG. 20 depicts the stimulation of endothelial sprouting from aortic rings observed with A) siEv70_2, B) Avastin and C) 5% Glucose.

Results: The aortic rings were scored, each group has 6 repeats and the average score of each group was compared. Both siEv70_2 and avastin inhibited aortic ring vessel sprouting. One-factor analysis of variance between siEv70_2 and 5% glucose groups showed significant deviation (P<0.001) (FIG. 20).

DNA-RNA Hybrid Strand and dsDNA Strand:

| sliRNA ID | | sliRNA sequence (5'→3') | |
|---|---|---|---|
| siEv70_6 | Sense strand | d(TAGGTACTTCGAGAAGCCTAGTATT) | (SEQ ID NO: 16) |
| | Antisense strand | UACUAGGCUUCUCGAAGUACCUA*dTdT* | (SEQ ID NO: 17) |
| siEv70_7 | Sense strand | d(CAATGCATTGAGAGGCCTGGATTT) | (SEQ ID NO: 18) |
| | Antisense strand | d(ATCCAGGCCTCTCAATGCATTGTT) | (SEQ ID NO: 19) |

Note:
siEv70_6 is DNA-RNA hybrid strand, siEv70_7 is dsDNA strand.

SMMC-7721 cells were cultured in DMEM (Invitrogen, USA) supplemented with 10% fetal bovine serum and trans- The length of double-stranded sliRNAs designed according to above sequence is less than 30 bp. The sliRNAs act as an exogenous ligand of membrane TLR3 to activate TLR3 signaling pathway, thereby inhibiting pathological angiogenesis-related diseases.

The sliRNA sequences are based on the nucleic acid template from 241 to 263 base pairs of the above, which has the following sequences:

```
Sense strand:
                                    (SEQ ID NO.: 14)
5'-UAGGUACUUCGAGAAGCCUAGUANn-3'

Antisense strand:
                                     (SEQ ID NO: 15)
5'-UACUAGGCUUCUCGAAGUACCUANn-3',
or:

Sense:
                                     (SEQ ID NO: 28)
5'-AGGUACUUCGAGAAGCCNn-3'

Antisense:
                                     (SEQ ID NO: 29)
5'-GGCUUCUCGAAGUACCUNn-3',
```

wherein, “N” is a base, which can be cytosine (C), guanine (G), adenine (A), uracil (U), deoxycytidine (dC), deoxyguanosine (dG), deoxyadenine (dA), or deoxythymidine (dT); “n” is an integer from 0 to 2.

In other words, the backbone sequences of the double-stranded sliRNA molecules are:

```
Sense strand:
                                      (SEQ ID NO: 2)
5'-UAGGUACUUCGAGAAGCCUAGUA-3'

Antisense strand:
                                      (SEQ ID NO: 3)
5'-UACUAGGCUUCUCGAAGUACCUA-3',
or the subsequences:

Sense:
                                     (SEQ ID NO: 30)
5'-AGGUACUUCGAGAAGCC-3'

Antisense:
                                     (SEQ ID NO: 31)
5'-GGCUUCUCGAAGUACCU-3'.
```

In a preferred embodiment, the sequence of the “Nn” at 3'end is the two deoxythymine dTdT.

Practically, alternative sequences of sliRNAs can be derived from the sequence SEQ ID NO: 1.

In order to verify the designed idea of this invention, the sliRNAs were designed by using the 5'UTR sequence of enterovirus EV70 (GenBank Accssion number: DQ201177) which is highly homologous targeting, and non-homologous with the human genome as template; and the negative control sliRNAs were designed by using the ORF and the non-conservative region of 3'UTR as template. VEGF antibody drug Avastin was used as a positive control. The following experimental protocols were designed to test the efficacy of the sliRNAs to treat pathological angiogenesis-related diseases.

1) The CNV mouse models were constructed with choroidal angiogenesis similar with the pathology of human AMD.
2) The method of fluorescence staining was used to evaluate the effects of the sliRNA on the CNV.
3) Quantitative RT-PCR technology was performed for comparing TLR3, VEGF, KDR, and IL12a gene expressions in the retinal tissue of the CNV mouse before and after the sliRNAs treatment.

We used mice as AMD animal model, and the drug formulations were the lyophilized powder of double-stranded specific sliRNA.

Example 2

AMD Animal Model Construction

Instruments, Reagents and Materials

Instruments: 5.4 mm Hand-held Contact Fundus Lens (Ocular Instruments, Bellevue, Wash., USA), Krypton Red Laser Photocoagulation (Lumenis, USA), Fluorescence Microscope (Eclipse TS10; Nikon, Japan), Slit Lamp Delivery System (Coherent, Novus 2000, USA), Confocal Laser Synchronized Angiography System (Hendeburg HRT II, Heidelberg, Germany), Karl Storz veterinary otoendoscope (STORZ, Germany), etc.

Animals: C57BL/6J mice, weight about 20-30 g.

Materials and Reagents: 0.3% Pentobarbital Sodium (45 mg/kg), tropicamide and phenylephrine (Alcon Fort Worth, Tex., USA). 10% Fluorescein Sodium (Guangxi Wuzhou Zhongheng Group Co. Ltd, China), 4% paraformaldehyde (Guoyao Group of Chemical Reagents, Beijing, China), 4',6'-diamidino-2-phenylindole (DAPI), phalloidin conjugated with Alexa Fluor 488 (Invitrogen-Molecular Probes, Eugene, Oreg.) and isolectin-B4 conjugated with Alexa Fluor 568 (Invitrogen-Molecular Probes, Eugene, Oreg.), etc.

CNV Animal Model Construction

CNV was induced by the method of laser photocoagulation. Briefly, C57BL/6J mice were anesthetized by an intraperitoneal (i.p.) injection with 45 mg/kg pentobarbital sodium. The pupils were dilated tropically with a mixture of 1% tropicamide and 2.5% phenylephrine. The laser photocoagulation were induced by a Krypton red laser source (wavelength 647.1 nm, laser power 260 mW, spot size 50 μm, and exposure time 0.05 s). The laser beam was delivered by the slit lamp delivery system with the assistance of 5.4 mm hand-held contact fundus lens in the front of the cornea. Two lesion spots were induced at the 12 and 6 o'clock positions around the optic disc, and in two papilla diameter distance from the optic disc. The generation of a bubble, indicating rupture of Bruch's membrane at the time of laser hitting, was considered a valid lesion. Lesions without bubble generation or with retina bleeding were excluded for further evaluation. The fundus photography was used to check the general condition of the laser burns, the fundus fluorescein angiography (FFA) and fluorescence staining of flat-mounted sclera-choroid/retinal pigment epithelium (RPE) complexes was to evaluate the CNV areas by masked operators Fundus Photography and Fundus Fluorescein Angiography (FFA)

Funduscopic photography was performed under systemic anesthesia (pentobarbital sodium, 0.3%, 45 mg/kg, i.p.) and pupil dilation (topical 1% tropicamide and 2.5% phenylephrine) using a Karl Storz veterinary otoendoscope coupled with a Nikon D90 digital camera.

FFA was performed with a confocal laser synchronized angiography system (Hendeburg HRT II, Heidelberg, Germany) after Funduscopic examination. Images were recorded at 2 min, 5 min, 15 min, and 30 min after intraperitoneal injection of fluorescein dye (10 mL/kg of 2% fluorescein sodium) and the angiography taken at 30 min was used to compare the efficacy of different treatments.

Fluorescence Staining

The whole eyes were enucleated after killing the animal. Flatmounted sclera-choroid/RPE complexes were stained by fluorescent-labeled isolectin-B4 (red) to quantify the area of CNV. The complexes were counterstained with DAPI (blue) for nucleus and phalloidin (green) for RPE layer.

At day 7 after laser-induced photocoagulation, mice were sacrificed by IP injection of overdosed pentobarbital sodium. The eyes were enucleated and immediately fixed in 4% paraformaldehyde in pH7.3 PBS for 1 hour. Under a biopsy microscope, the anterior segment was removed, and the neurosensory retina was detached and separated from the optic nerve head. The remaining eyecup was incubated with a 20 ng/μL, solution of DAPI, a 10 ng/μL solution of isolectin-B4, and a 0.002 U/μl solution of phalloidin in a humidified chamber at 4° C. with gentle shaking for 4 hours. Four radial cuts were made toward the optic nerve head to flatmount the sclera-choroid/RPE complexes on glass slide. The samples were covered and, sealed for microscopic analysis.

Fluorescence Microscopy Examination: The images of CNV complexes were collected in the blue (DAPI), red (isolectin B4), and green (phalloidin) channels of fluorescence. All images were recorded using a resolution of 1392× 1040 pixels and a depth of 8 bits in all channels.

Figure 2:
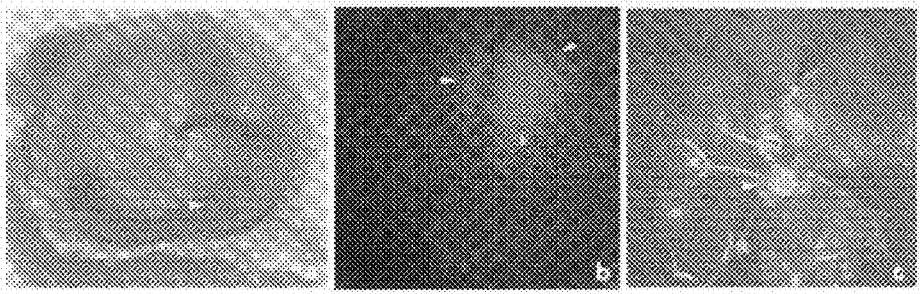
FIG. 2*a* depicts a gross anatomy of the eye of CNV mouse model that was induced by laser photocoagulation in C57BL/6J mice. The arrow on the right bottom indicates the laser spot close to the optic disc.
FIG. 2*b* shows the fundus photographs at 5 min after krypton laser photocoagulation. The arrows indicate the laser spots and retinal edema.
FIG. 2*c* shows a flatmount micro-photograph of sclera-choroid/RPE under microscope (magnification 100×). The arrow indicates a laser spot close to the optic nerve.
Figure 3:
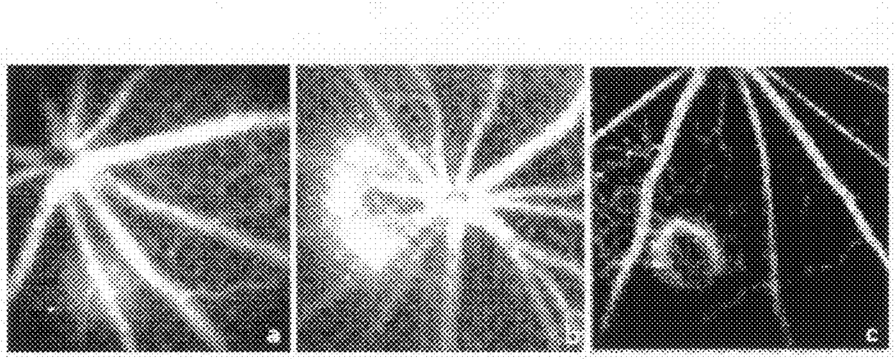
FIG. 3 shows the micrographs recorded by a Confocal Laser Synchronized Angiography System: fundus fluorescein angiography (FFA) examination shows the vascular changes of C57BL/6J mice after krypton laser photocoagulation. Laser spot was observed on discoid fluorescein leakage 7 days after photocoagulation (FIG. 3*a*); Laser spot clearly visible fluorescein leakage 14 days after photocoagulation, the arrow indicates the photocoagulation sites (FIG. 3*b*). No laser spot fluorescence leakage was observed and scarring occurred 28 days after photocoagulation (FIG. 3*c*).
Figure 4:
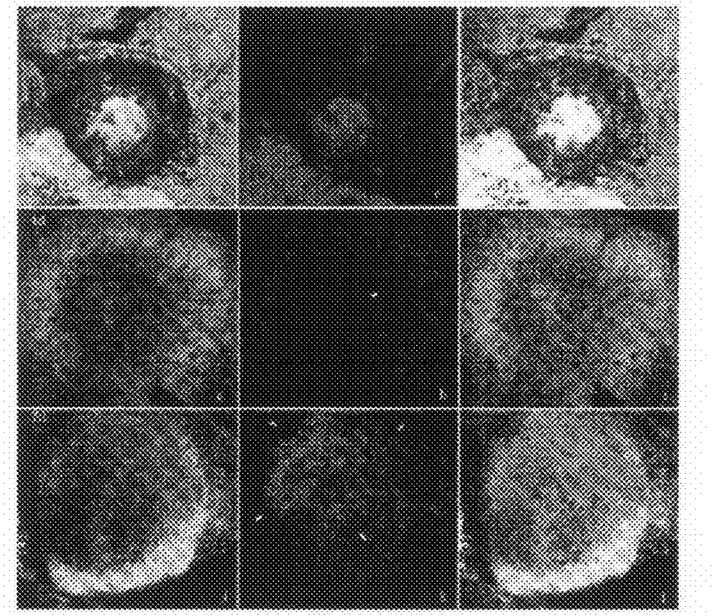
FIG. 4 shows the fluorescence micrographs of choroidal flatmount observed under the microscope (magnification 100×). The laser-induced burns were in ring-shape lesions presented in FIG. 4*d-f*. On day 4 after photocoagulation, some cell debris and nuclear fragments appeared inside the lesions (FIG. 4*g-i*). On day 7, the CNV network stained by isolectin-B4 could be observed in the laser damage zone. The RPE cells covered the areas of CNV complex (FIG. 4*j-l*). The CNV areas on day 14 and on day 28 were not significantly different, but both of them were significantly increased comparing with CNV area on day 7.

Validation of the Mice CNV Model by Fundus Photography, FFA and Fluorescence Staining In normal retina of B6 mouse, the RPE cells were in hexagonal arrangement on the top of sclera-choroid/RPE complexes flatmount as stained by phalloidin (FIG. 1*a*); the signal from isolectin-B4 was not observed (FIG. 1*b*); DAPI labeled nucleus of RPE cells can be identified by the overlay image (FIG. 1*c*). The images of fundus photography showed the laser burn on retina as a chalk-like spot, which was considered as acute edema (FIG. 2). On day 4, the gray-white edema was showed clearly. On day 7, the retinal edema was still visible and the blood leakage began to be absorbed. On day 14, the retinal edema disappeared and most of the leakage was absorbed. On day 28, a scar was formed with hyperpigmentation. In FFA examination, fluorescein hot spot was observed at photocoagulation site 5 min after laser photocoagulation. On day 7 after photocoagulation, a disc-shaped fluorescein leakage appeared (FIG. 3*a*). On day 14, fluorescein leakage gradually increased at the spot (FIG. 3*b*). On day 28, less fluorescein leakage at the laser-induced-spot was observed and a scar was formed (FIG. 3*c*). The laser-induced burns were in ring-shape lesions presented in FIG. 4*d-f*. On day 4 after photocoagulation, some cell debris and nuclear fragments appeared inside the lesions (FIG. 4*g-i*). On day 7, the CNV network stained by isolectin-B4 could be observed in the laser damage zone. The RPE cells covered the areas of CNV complex (FIG. 4*j-l*). The average CNV areas were 8.03±0.53×$10^3$ μ$m^2$, 16.69±4.78×$10^3$ μ$m^2$, and 15.23±4.47× $10^3$ μ$m^2$ on day 7, day 14, and day 28, respectively. The CNV areas on day 14 and on day 28 were not significantly different, but both of them were significantly increased comparing with CNV area on day 7.

This example indicates that FFA and fluorescence staining can be used to qualitatively and quantitatively evaluate the Krypton laser-induced CNV. These methods can provide reliable data for the efficacy study of anti-angiogenesis drugs.

Example 3 sliRNA Preparation and Intravitreal Injection for CNV Model

Instruments, Reagents and Materials

Oligo Synthesizer (GE, USA), Hamilton Micro-Syringe (Hamilton Co., Reno, Nev., USA).

Materials and Reagents: sliRNA (Biomics Biotech, China), Avastin (Genentech, USA), 5% Glucose Solution (Biomics Biotech, China).

sliRNA Sequence:

| sliRNA ID | | sliRNA sequence (5'→3') | SEQ ID NO: |
|---|---|---|---|
| siEv70_1 | Sense | CAAUGCAUUGAGAGGCCUGGAU*dTdT* | 4 |
| | Antisense | AUCCAGGCCUCUCAAUGCAUUG*dTdT* | 5 |
| siEv70_2* | Sense | UAGGUACUUCGAGAAGCCUAGUA*dTdT* | 6 |
| | Antisense | UACUAGGCUUCUCGAAGUACCUA*dTdT* | 7 |
| siEv70_3 | Sense | CCUGAGAGUCCUCCGGCCCCU*dTdT* | 8 |
| | Antisense | AGGGGCCGGAGGACUCUCAGG*dTdT* | 9 |
| siEv70_4 | Sense | AGAGAGAAAGUAGAGAAGGGC*dTdT* | 10 |
| | Antisense | GCCCUUCUCUACUUUCUCUCU*dTdT* | 11 |
| siEv70_5 | Sense | UAGGAACCCAAGAACCCCUCC*dTdT* | 12 |
| | Antisense | GGAGGGGUUCUUGGGUUCCUA*dTdT* | 13 |

*siEv70_2 is a highly conserved sequence of enterovirus 70 (EV70). siEv70_1, siEv70_3, siEv70_4 and siEv70_5 are non-conserved sequence. The sequences were obtained from GenBank Accssion number: DQ201177.

sliRNA Design

The 5'UTR region of human enterovirus 70 (EV70) is highly conserved in enterovirus families and has no homology with human genome after blasted in NCBI nucleic acid sequence data bank. We designed the sliRNA sequences in consideration of the stabilities of sliRNA secondary structure, Tm value and GC content. We chose the conserved domain of viral genome as a template to design sliRNA with targeting TLR3 and non-conserved region of the ORF and 3'UTR of viral genome as templates to design the negative control sliRNAs.

sliRNA Chemical Synthesis

The sense and antisense strand of sliRNAs were synthesized and purified by Oligo Synthesizer (GE, USA), the sense and complementarily antisense strand were annealed to form sliRNA duplexes and lyophilized 1 OD in each tube.

Intravitreal Injection of sliRNA

The lyophilized powder of sliRNAs duplex were dissolved in 5% glucose solution to give a solution with the concentration at 1-2 μg/μL. One μL of sliRNA was intravitreally injected into both eyes of the CNV model. Avastin (1 μL/eye, 25 mg/mL), a VEGF antibody drug, was intravitreally injected as the positive control. The detail procedures of injection include: 1) puncture of anterior chamber; 2) release some aqueous humor; 3) inject sliRNA solution into the vitreous cavity using a 2.5 μL, Hamilton Syringe (Hamilton Co., Reno, Nev.) and a 32-gauge needle at the position of 1 mm away from the limbus under a dissecting microscope.

At different time points, Fundus Photography, FFA and fluorescence staining were used to compare the CNV after the different treatments. ImageJ software was used to quantitate the density and area of CNV.

Example 4

Screening sliRNA Targets by Fluorescence Staining

Instruments, Reagents, and Materials

Instruments: 5.4 mm Hand-held Contact Fundus Lens (Ocular Instruments, Bellevue, Wash., USA), Krypton Red Laser Photocoagulation (Lumenis, USA), Fluorescence Microscope (Eclipse TS10; Nikon, Japan), Slit Lamp Delivery System (Coherent, Novus 2000, USA), Confocal Laser Synchronized Angiography System (Hendeburg HRT II, Heidelberg, Germany), etc.

Reagents and Materials: 0.3% Pentobarbital Sodium (45 mg/kg), Proparacaine Hydrochloride (S.A.ALCON-COUVERUR N.V), 1% Tropicamide (Santen, Osaka, Japan), 10% Fluorescein Sodium (Guangxi Wuzhou Zhongheng Group Co. Ltd), 4% paraformaldehyde (Guoyao Group of Chemical Reagents, Beijing, China), etc.

Fluorescence dyes: 4',6'-diamidino-2-phenylindole (DAPI), phalloidin conjugated with Alexa Fluor 488 (Invitrogen-Molecular Probes, Eugene, Oreg.) and isolectin-B4 conjugated with Alexa Fluor 568 (Invitrogen-Molecular Probes, Eugene, Oreg.), etc.

Tissue Flatmount and Fluorescence Staining

The eyeballs were enucleated for flatmount of sclera-choroid/RPE complex. The nucleus, endothelial cells, and PRE were stained with fluorescent dyes of DAPI (Blue), isolectin-B4 (Red), and phalloidin (Green) respectively.

Sclera-choroid/RPE Flatmount and Staining: The mice were executed at 5 min, on day 4, day 7, day 14 and day 28 after laser photocoagulation of retina. The eyes were enucleated and immediately fixed in 4% paraformaldehyde in pH7.3 PBS for 1 h. Under a biopsy microscope, the anterior segment was removed, and the neurosensory retina was detached and separated from the optic nerve head. The remaining eyecup was incubated with a 20 ng/μl, solution of DAPI, a 10 ng/μl solution of isolectin-$B_4$, and a 0.002 U/μl solution of phalloidin in a humidified chamber at 4° C. with gentle shaking for 4 hours. Four radial cuts were made toward the optic nerve head to flatmount the sclera-choroid/RPE complexes on glass slide. The samples were covered and sealed for microscopic analysis.

Fluorescence Microscopy Examination: The morphology of CNV was observed under fluorescence microscope. The images of CNV complexes were obtained using the blue (DAPI), red (isolectin B4), and green (phalloidin) channels respectively. All images were recorded using a resolution of 1392×1040 pixels and a depth of 8 bits in all channels.

Result Analysis

The samples from the day 7 after laser coagulation were used for comparison (Campos et al., 2006). The nucleus, endothelial cells and RPE were labeled by fluorescent DAPI (Blue), isolectin-B4 (Red), and phalloidin (Green) respectively (FIG. 5-12)

Figure 5:
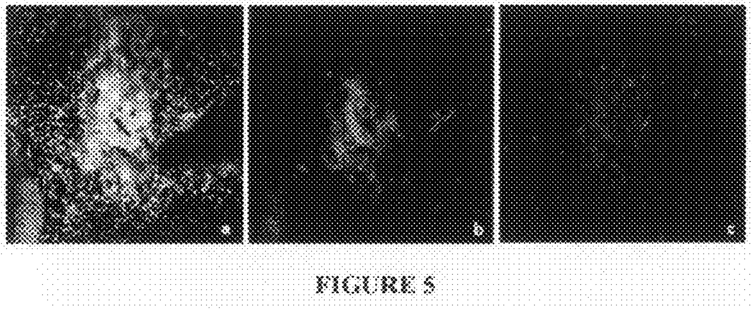
FIG. 5 shows the fluorescence micrographs of choroidal flatmount observed under the microscope (magnification 100×). The samples from the day 7 after laser coagulation were used for comparison. The nucleus, endothelial cells and RPE were labeled by fluorescent DAPI (Blue), isolectin-B4 (Red), and phalloidin (Green) respectively.
Figure 6:
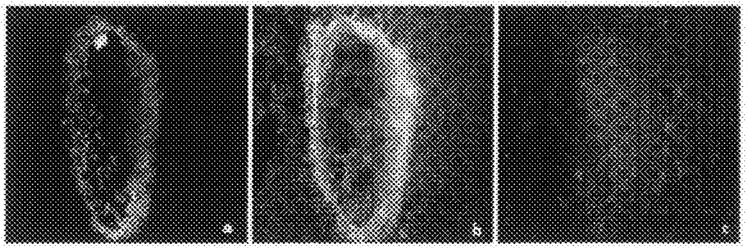
FIG. 6 shows the fluorescence micrographs of choroidal flatmount observed under the microscope (magnification 100×). The samples from the day 7 after laser coagulation treated by 5% glucose solution were used for comparison. The nucleus, endothelial cells and RPE were labeled by fluorescent DAPI (Blue), isolectin-B4 (Red), and phalloidin (Green) respectively.
Figure 7:
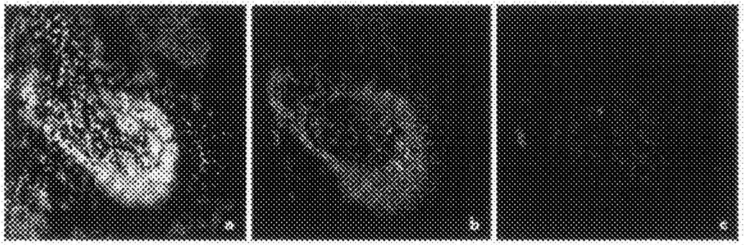
FIG. 7 shows the fluorescence micrographs of choroidal flatmount observed under the microscope (magnification 100×). The samples from the day 7 after laser coagulation treated by Avastin were used for comparison. The nucleus, endothelial cells and RPE were labeled by fluorescent DAPI (Blue), isolectin-B4 (Red), and phalloidin (Green) respectively.
Figure 8:
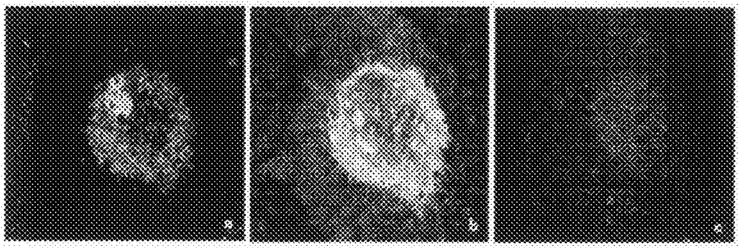
FIG. 8 shows the fluorescence micrographs of choroidal flatmount observed under the microscope (magnification 100×). The samples from the day 7 after laser coagulation treated by siEv70_1 were used for comparison. The nucleus, endothelial cells and RPE were labeled by fluorescent DAPI (Blue), isolectin-B4 (Red), and phalloidin (Green) respectively.
Figure 9:
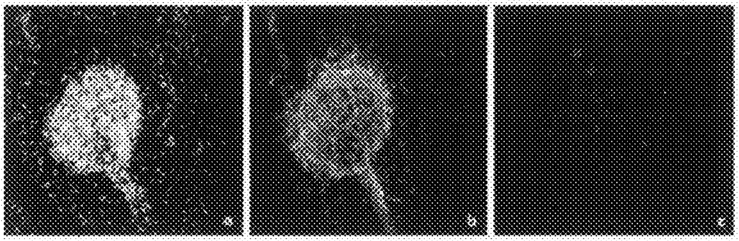
FIG. 9 shows the fluorescence micrographs of choroidal flatmount observed under the microscope (magnification 100×). The samples from the day 7 after laser coagulation treated by siEv70_2 were used for comparison. The nucleus, endothelial cells and RPE were labeled by fluorescent DAPI (Blue), isolectin-B4 (Red), and phalloidin (Green) respectively.
Figure 10:
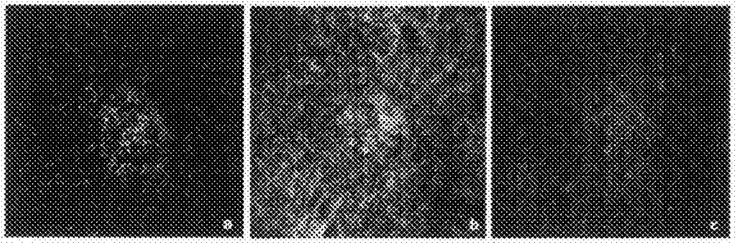
FIG. 10 shows the fluorescence micrographs of choroidal flatmount observed under the microscope (magnification 100×). The samples from the day 7 after laser coagulation treated by siEv70_3 were used for comparison. The nucleus, endothelial cells and RPE were labeled by fluorescent DAPI (Blue), isolectin-B4 (Red), and phalloidin (Green) respectively.
Figure 11:
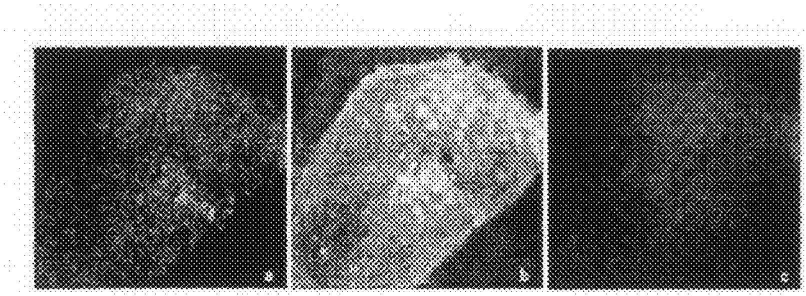
FIG. 11 shows the fluorescence micrographs of choroidal flatmount observed under the microscope (magnification 100×). The samples from the day 7 after laser coagulation treated by siEv70_4 were used for comparison. The nucleus, endothelial cells and RPE were labeled by fluorescent DAPI (Blue), isolectin-B4 (Red), and phalloidin (Green) respectively.
Figure 12:
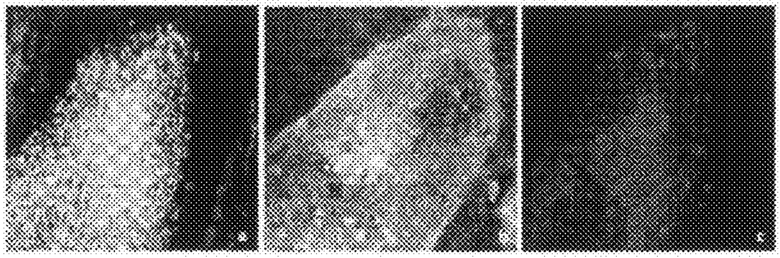
FIG. 12 shows the fluorescence micrographs of choroidal flatmount observed under the microscope (magnification 100×). The samples from the day 7 after laser coagulation treated by siEv70_5 were used for comparison. The nucleus, endothelial cells and RPE were labeled by fluorescent DAPI (Blue), isolectin-B4 (Red), and phalloidin (Green) respectively.

Endothelial cells were stained by isolectin-B4 (Red) for the evaluation of neovascularization (CNV), the images form the red channel were used to evaluate the efficacy of the inhibition of CNV treated by sliRNAs and Avastin. The areas of CNV, in the siEv70__2 treated group (FIG. 9) and positive control group Avastin (FIG. 7), were reduced obviously, comparing to the negative control group (FIGS. 5 and 6). No inhibition effect of CNV was observed in other groups (FIG. 8, FIG. 10, FIG. 11, and FIG. 12).

Figure 13:
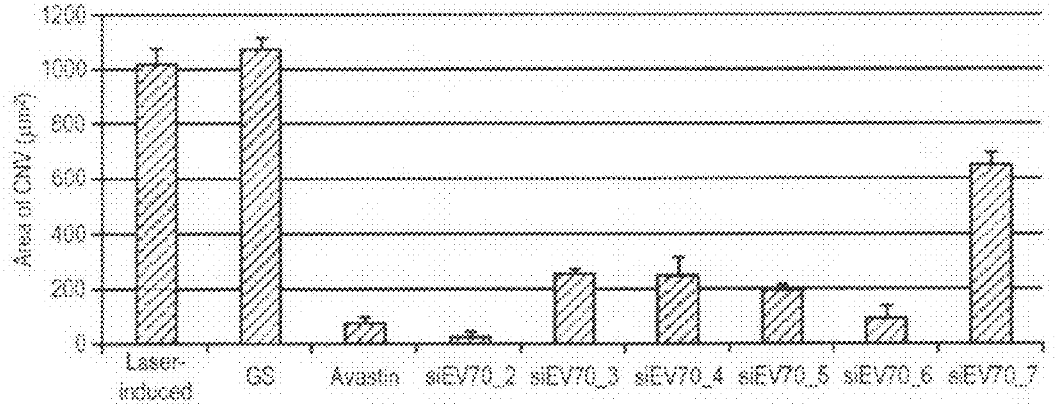
FIG. 13 shows ImageJ photo analysis software was used to quantify the average area of CNV, in which each treated group were less than negative control; the siEv70_2 treated group was obviously further less than other treated groups.

ImageJ photo analysis software was used to quantify the average area of CNV. The average CNV of each treated group were less than negative control; the siEv70__2 treated group was obviously further less than other treated groups. (FIG. 13)

Example 5

Quantitative RT-PCR Analysis of TLR3 Activation

Instruments, Reagents and Materials iQ5 real-time PCR detection system (Bio-Rad, USA), Centrifuge (Eppendorf, Germany), glass-Teflon, and etc.

Reagents and Materials: 96-well qPCR plate (Bio-Rad, USA), RISO™ RNA isolation reagent (Biomics Biotech, China), SYBR Green I (Invitrogen, USA), Icycler iQ calibration solutions (Bio-Rad, USA), AMV Reverse kit (Promega, USA), Taq DNA polymerase (Biomics Biotech, China), Avastin (Genentech, USA) and etc.

Primers. Used for Quantitative RT-PCR Analysis:

| Detected Gene | Accession No. | 5'&3'primer | Primer sequence (5'→3') | Amplicon |
|---|---|---|---|---|
| Mus musculus interleukin 12a (Il12a) | NM_008351 | 5'IL12a_QF | CTGGAACTACACAAGAACGAGAG (SEQ ID NO: 20) | 135 bp |
| | | 3'IL12a_QR | CTTCAAGTCCTCATAGATGCTACC (SEQ ID NO: 21) | |
| Mus musculus toll-like receptor 3 (Tlr3) | NM_126166 | 5'TLR3_QF | TTTAGAGTCCAACGGCTTAG (SEQ ID NO: 22) | 150 bp |
| | | 3'TLR3_QR | TGGAGGTTCAGTGACCTTAG (SEQ ID NO: 23) | |
| Mus musculus vascular endothelial growth factor A (Vegfa) | NM_001025250.2 NM_001025257.2 NM_009505.3 | 5'VEGFA_QF | GACATCTTCCAGGAGTACC (SEQ ID NO: 24) | 197 bp |
| | | 3'VEGFA_QR | TGCTGTAGGAAGCTCATCTC (SEQ ID NO: 25) | |
| Mus musculus glyceraldehyde- | NM_008084.2 | 5'GD_QF | GTATGACTCCACTCACGGCAAA (SEQ ID NO: 26) | 101 bp |

-continued

| Detected Gene | Accession No. | 5'&3'primer | Primer sequence (5'→3') | Amplicon |
|---|---|---|---|---|
| 3-phosphate dehydrogenase (Gapdh) | | 3'GD_QR | GGTCTCGCTCCTGGAAGATG (SEQ ID NO: 27) | |

CNV Mouse Model Treated vs. Untreated Groups:

| No. | Group ID. | Treatment methods |
|---|---|---|
| 1 | Normal | Untreated |
| 2 | Laser-induced | Untreated |
| 3 | Avastin | Avastin (25 mg/mL, 1 μL) |
| 4 | GS | Glucose Solution (5% (m/v), 1 μL) |
| 5 | siEv70_2 | sliRNA (1 μg/μL, 1 μL) |
| 6 | siEv70_3 | sliRNA (1 μg/μL, 1 μL) |
| 7 | siEv70_4 | sliRNA (1 μg/μL, 1 μL) |
| 8 | siEv70_5 | sliRNA (1 μg/μL, 1 μL) |

Quantitative RT-PCR

RNA Isolation from Eyes of CNV Mouse Model:

The whole eye was homogenized in 1 mL RISO Reagent and incubated at 15-30° C. for 5 min to dissociate the nucleoprotein complexes. 0.2 mL of chloroform was added, followed by hand shaking for 15 s. The samples were allowed to stand at room temperature for 2 to 15 min, followed by centrifugation at 12,000 rpm at 4° C. for 15 min. After centrifugation, the mixture will form three phases: a bottom-phase in red containing phenol-chloroform extract; a medium-phase; and a colorless top aqueous phase. The RNA remained exclusively in the aqueous phase. The 0.4 mL of aqueous phase was transferred to a clean tube and the RNA was precipitated by adding 0.4 mL isopropyl alcohol. The mixture was centrifuge at 12,000 rpm, at 4° C. for 10 min to form RNA pellet. The RNA pellet was washed with 1 mL of 75% ethanol and the mixture was centrifuge at 12,000 rpm, at 4° C. for 10 min to form RNA pellet again. The pellet was dried in air-dry for 5-10 min after discharging the supernatant. The purity and quantity of RNA were determined at the absorption of 260-280 nm. Further agarose-formaldehyde electrophoresis was performed for analysis of RNA integrity and purity.

The First Strand cDNA Synthesis by Reverse Transcriptase: The first strand cDNA was synthesized from the extracted RNA using AMV reverse transcriptase. One μg of RNA template was heated at 70° C. for 10 min, and then allowed to stand on ice for 5 min. The reaction mix contained: 5 μL of the 5× Reverse Transcription Buffer, 1 μg of Oligo $(dT)_{15}$, 2.5 μL of dNTP, 40 units of RNA Ribonuclease Inhibitor and 30 units of AMV Reverse Transcriptase. A final reaction volume was adjusted to 25 μl by adding RNase free water. The reaction was incubated at 42° C. for 1 hr and terminated by adding $ddH_2O$ to the volume of 200 μL.

Quantitative RT-PCR: The mRNA levels of three genes: TLR3, IL12a and VEGF were measured using gene specific primers using housekeeping gene GAPDH as the loading control. The 25 reaction mix contained: 5 μL template cDNA, 2.5 μL 10×PCR Buffer, 0.5 μL dNTP (10 mM each), 0.5 μL 5'primer (10 μM), 0.5 μL 3'primer (10 μM), 1.5 μL SYBR Green I (2000× diluted), 0.25 μL Icycler iQ calibration solutions (100× diluted) and 0.25 μL Taq DNA polymerase, 14 μL $ddH_2O$. PCR reaction was repeated for 45 cycles as preheating at 95° C. for 5 min, denaturing at 95° C. for 20 s, annealing at 60° C. for 30 s, and extension at 72° C. for 30 s.

Figure 14:
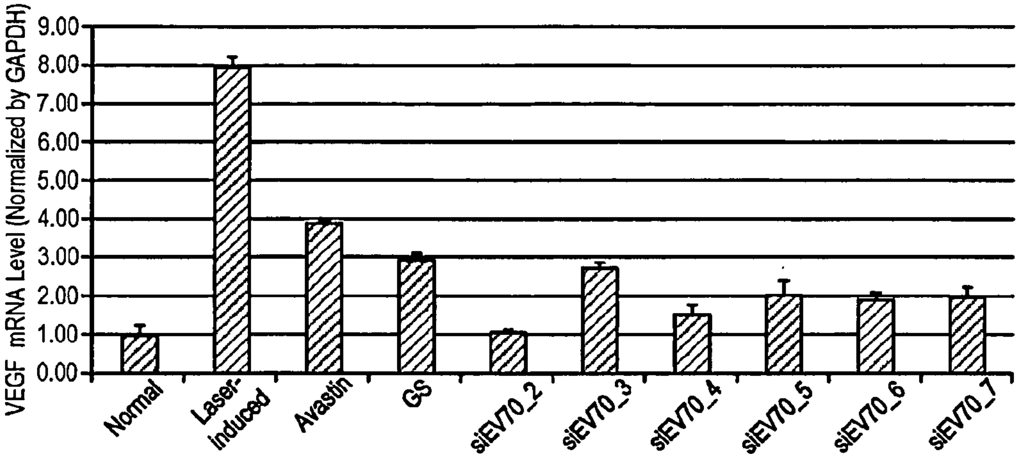
FIG. 14 shows the VEGF mRNA level of each treated groups: VEGF mRNA level in the eyes of laser-induced without treatment was significantly higher than those of the treated groups and among the treated groups the VEGF mRNA level in siEv70_2 treated group was the lowest with statistical significance.

Result Analysis:

FIG. 14 shows the VEGF mRNA level in each treated groups: The level of VEGF mRNA in the eyes of laser-induced without treatment was significantly higher than those of the treated groups among the treated groups; the level of VEGF mRNA in siEv70_2 treated group was the lowest with statistical significance.

Figure 15:
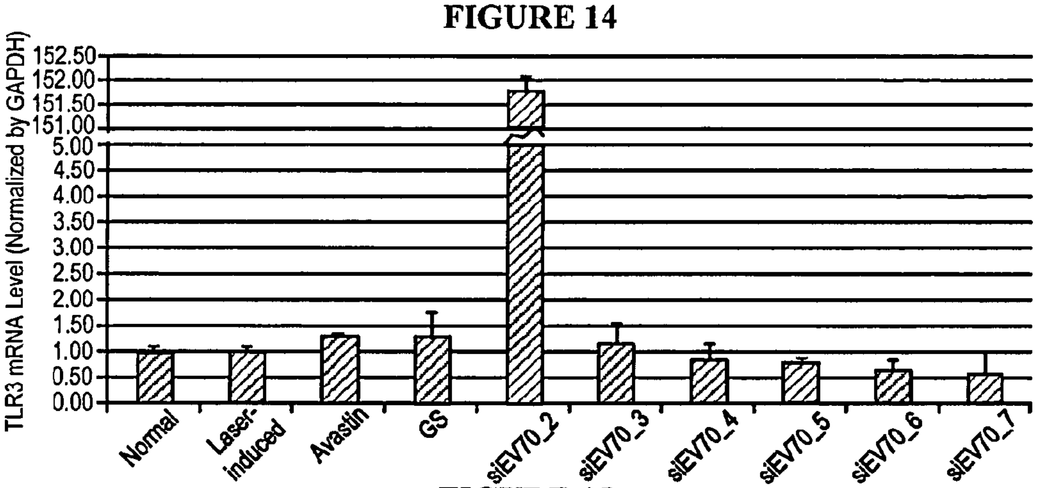
FIG. 15 shows the real-time PCR measurement of TLR3 mRNA level of each treated group: The level of TLR3 mRNA in siEv70_2 treated group was higher than the control group. Other treated groups did not have significant differences from the normal control group. The activation of TLR3 by siEv70_6 (DNA: RNA hybrid) is less than the dsRNA with same sequence (siEv70_2).

FIG. 15 shows the TLR3 mRNA level of each treated group: The level of TLR3 mRNA in siEv70_2 treated group was higher than the normal control group. And other treated groups did not have significant differences from the normal control group.

Figure 16:
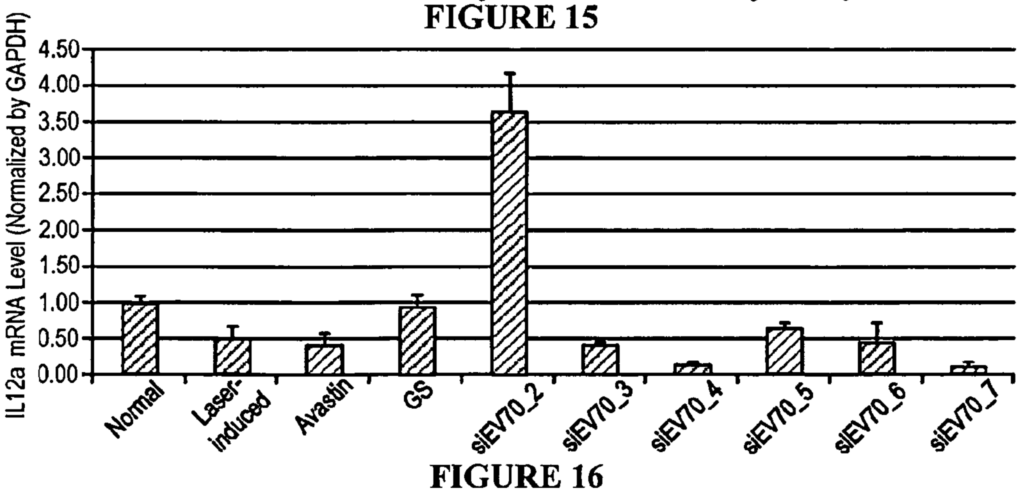
FIG. 16 shows the real-time PCR measurement of IL12a mRNA level of each treated group: The level of IL-12a mRNA in siEv70_2 treated group was higher than the normal control group. And other treated groups did not have significant changes in comparison with the normal control group. The activation of IL12 by siEv70_6 (DNA: RNA hybrid) is less than the dsRNA with same sequence (siEv70_2).

FIG. 16 shows the IL12a mRNA level of each treated group: The level of IL12a mRNA in siEv70_2 treated group was higher than the normal control group. And other treated groups did not have significant changes in comparison with the normal control group.

Although the sliRNA was designed from the highly conserved domain of enteroviral genome at 241-263 nt and its anti-AMD efficiency was confirmed in C57BL/6J mice CNV model, the basic principle of design can be expanded to any species of viral highly conserved domains and with any kinds of modifications as well as applications.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 6

CNV Suppression by siEv70_2 via TLR3 in Dose-Dependent Manner

The detailed procedures of AMD animal model construction, sliRNAs preparation, intravitreal injection, choroid flatmount and fluorescence staining were same as provided in Example 1-4.

The lyophilized powder of sliRNAs duplex were dissolved in 5% glucose solution to a final concentration of 0.2 μg/μL, 2 μg/μL and 10 μg/μL, respectively. Forty-eight hours after laser injury, 1 μL of sliRNA was intravitreally injected into both eyes of CNV mice. Polyinosine-polycytidylic acid (poly (I:C)) (1 μL/eye, 0.2 μg/μL) and 0.5% (m/v) glucose solution were intravitreally injected as positive control and negative control, respectively. Poly(I:C) is a synthetic analog of double-stranded RNA (dsRNA), which is present in some viruses. It is known to interact with TLR3, which is expressed in the membrane of some mammalian cells, activating Nuclear Factor κB (NF-κB) pathway to produce type 1 interferons (IFNs) and cytokines (Alexopoulou et al. Nature, 2001; 413, 732-8).

Twelve days after laser-induced photocoagulation, mice were sacrificed and eyes were enucleated. All of the eyecups were flatmounted and stained with specified fluorescein dyes. The density and areas of CNV were calculated with Image J software.

CNV Mouse Model Treated vs. Untreated Groups:

| No. | Group ID. | Treatment methods |
|---|---|---|
| 1 | Untreated | Laser-induced with no injection |
| 2 | GS | 5% (m/v) Glucose Solution |
| 3 | poly(I:C) | poly(I:C) (0.2 μg/eye) (InvivoGen, USA) |
| 4 | siEv70_2 (0.2 μg) | siEv70_2 (0.2 μg/eye) |
| 5 | siEv70_2 (2 μg) | siEv70_2 (2 μg/eye) |
| 6 | siEv70_2 (10 μg) | siEv70_2 (10 μg/eye) |

Result Analysis:

Dose-effect relationship of siEv70_2 injection for suppression of laser-induced CNV was evaluated in CNV mice. Negative controls were untreated or vehicle GS injected, and positive control was injected with poly(I:C).

Figure 21:
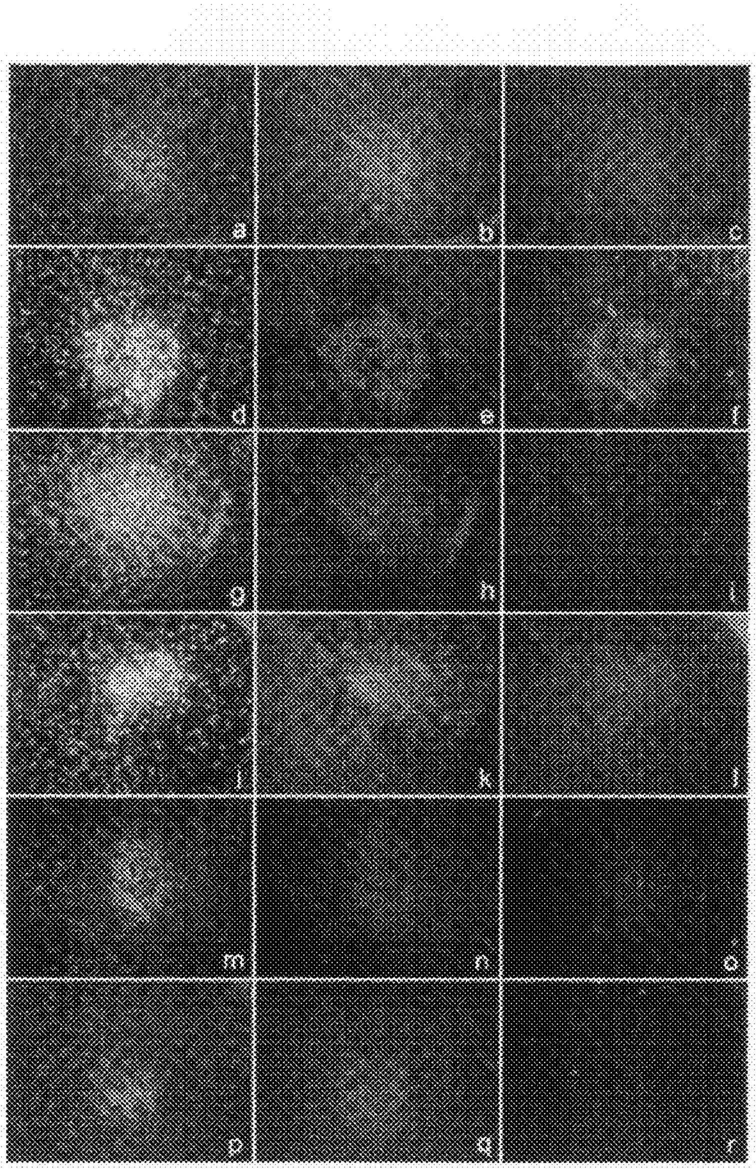
FIG. 21 shows the fluorescence micrographs of choroidal flatmount observed under the microscope (magnification 100×). Dose-effect relationship of siEv70_2 injection for suppression of laser-induced CNV was evaluated in CNV mice. The nucleus, endothelial cells and RPE were labeled by fluorescent DAPI (Blue), isolectin-B4 (Red), and phalloidin (Green) respectively. The areas of CNV, in the siEv70_2 (2 μg) (FIG. 21*m-o*), siEv70_2 (10 μg) (FIG. 21*p-r*) treated group and poly(I:C) positive control group (FIG. 21*g-i*), were reduced obviously, comparing to untreated group (FIG. 21*a-c*) and negative control group (FIG. 21*d-f*). No inhibition effect of CNV was observed in the siEv70_2 (0.2 μg) treated group (FIG. 21*j-l*).
Figure 22:
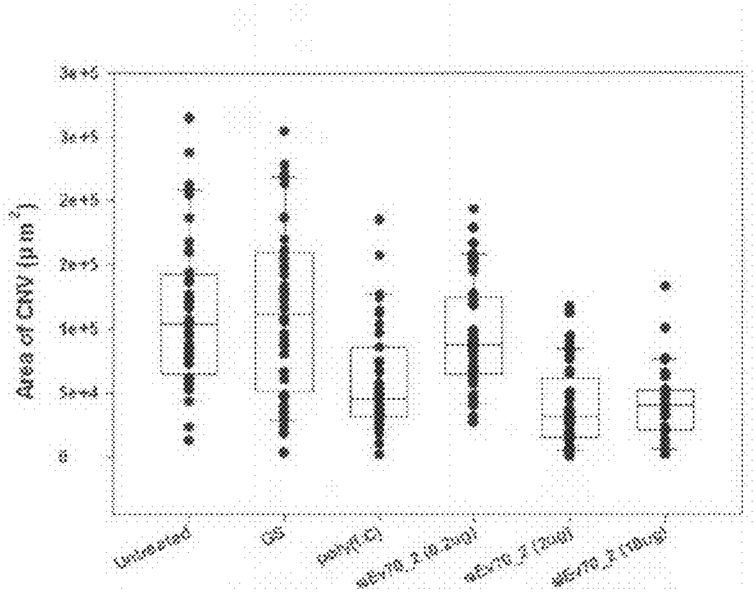
FIG. 22 shows the Box-and-whisker plot of the areas of CNV. The y-axis represents CNV areas expressed in square microns ($\mu m^2$). Each dot corresponds to one CNV lesion (total=247), including siEv70_2 (0.2 μg) (n=41), siEv70_2 (2 μg) (n=52), siEv70_2 (10 μg) (n=35), poly(I:C) (n=39), GS (n=40) and untreated (n=40).

Representative images as shown in FIG. 21, the endothelial cells were stained by isolectin-B4 (Red) for the evaluation of neovascularization (CNV), the images form the red channel were used to evaluate the efficacy of the inhibition of CNV treated by sliRNAs and poly(I:C). The areas of CNV, in the siEv70_2 (2 μg) (FIG. 21*m-o*), siEv70_2 (10 μg) (FIG. 21*p-r*) treated group and poly(I:C) positive control group (FIG. 21*g-i*), were reduced obviously, comparing to untreated group (FIG. 21*a-c*) and negative control group (FIG. 21*d-f*). No inhibition effect of CNV was observed in the siEv70_2 (0.2 μg) treated group (FIG. 21*j-l*).

Statistical analysis showed that siEv70_2 (2 μg), siEv70_2 (10 μg) and poly(I:C) significantly suppressed CNV by 66.0% ($P<0.001$), 64.0% ($P<0.001$), 47% ($P<0.001$), respectively, compared to untreated group. However, siEv70_2 (0.2 μg/eye) and GS treated groups had no significant CNV suppression effects, compared to untreated group.

Example 7

CNV Suppression by BM01 via TLR3

BM01 is the subsequence of siEv70_2, which has the following sequences:

```
Sense:
                                        (SEQ ID NO: 32)
5'-AGGUACUUCGAGAAGCCdTdT-3'

Antisense:
                                        (SEQ ID NO: 33)
5'-GGCUUCUCGAAGUACCUdTdT-3'.
```

The detailed procedures of AMD animal model construction, sliRNA preparation, intravitreal injection, choroid flatmount and fluorescence staining were same as mentioned in Example 1-4. The lyophilized powder of sliRNA duplex was dissolved in 5% glucose solution to a final concentration of 2 μg/μL. Forty-eight hours after laser injury, 1 μL of sliRNA was intravitreally injected into both eyes of the CNV mice. Poly(I:C) (1 μL/eye, 0.2 μg/μL) and 0.5% (m/v) glucose solution were intravitreally injected as positive control and negative control, respectively.

Twelve days after laser-induced photocoagulation, mice were sacrificed and eyes were enucleated. All of the eyecups were flat mounted and stained with specified fluorescein dyes. The density and areas of CNV were calculated with Image J software.

CNV Mouse Model Treated vs. Untreated Groups:

| No. | Group ID. | Treatment methods |
|---|---|---|
| 1 | Untreated | Laser-induced with no injection |
| 2 | GS | 5% (m/v) Glucose Solution |
| 3 | poly(I:C) | poly(I:C) (0.2 μg/eye) (InvivoGen, USA) |
| 4 | BM01 | BM01 (2 μg/eye) (Biomics Biotech, China) |

Figure 23:
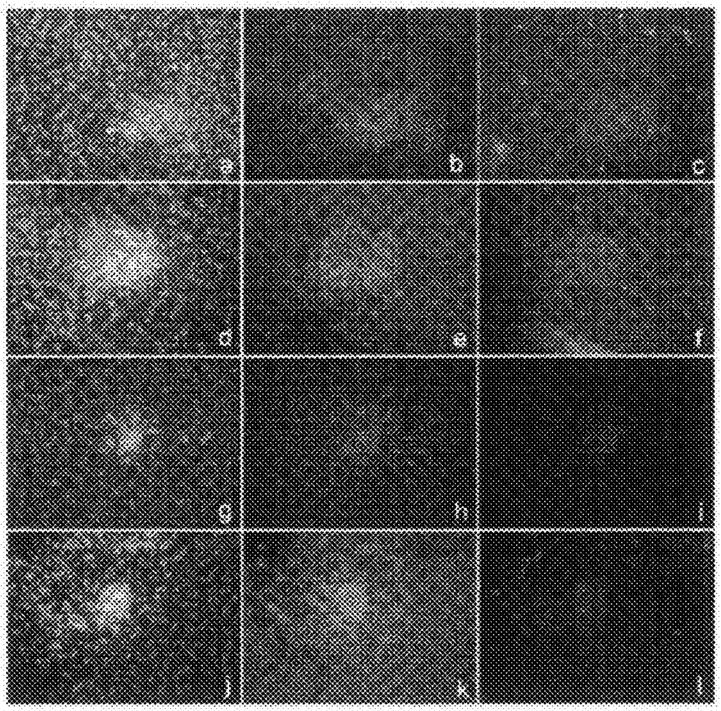
FIG. 23 shows the fluorescence micrographs of choroidal flatmount observed under the microscope (magnification 100×). Intravitreal injection of BM01 was evaluated for the effects of CNV suppression in laser-induced CNV mice. The nucleus, endothelial cells and RPE were labeled by fluorescent DAPI (Blue), isolectin-B4 (Red), and phalloidin (Green) respectively. The CNV were suppressed obviously in the BM01 and poly(I:C) treated group (FIG. 23*j-l* and FIG. 23*g-i*), comparing to untreated group (FIG. 23*a-c*) and negative control group (FIG. 23*d-f*).
Figure 24:
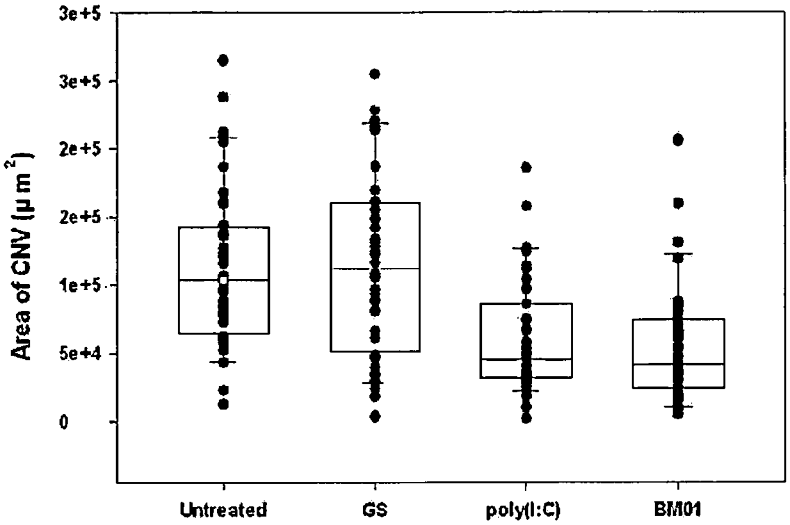
FIG. 24 shows the Box-and-whisker plot of the areas of CNV. The y-axis represents CNV areas expressed in square microns ($\mu m^2$). Each dot corresponds to one CNV lesion (total=155), including BM01 (n=36), poly(I:C) (n=39), GS (n=40) and untreated (n=40).

Result Analysis:

Intravitreal injection of BM01 was evaluated for the effects of CNV suppression in laser-induced CNV mice. Negative control were untreated or vehicle GS injected, and positive controls were injected with poly(I:C). Representative images (FIG. 23) illustrated that the areas of CNV were suppressed obviously in the BM01 and poly(I:C) treated group (FIG. 23*j-l* and FIG. 23*g-i*), comparing to untreated group (FIG. 23*a-c*) and negative control group (FIG. 23*d-f*).

Statistical analysis showed that BM01 and poly(I:C) suppressed CNV by 52.0% ($P<0.001$) and 47% ($P<0.001$) respectively, compared to untreated group.

What is claimed is:

1. An sliRNA for modulating a Toll-like Receptor (TLR), comprising a nucleotide sequence that is 14-25 nucleotides in length and at least 90% identical to a fragment of a highly conserved domain of a viral genome sequence of a picornavirus, wherein the sliRNA has a GC content of at least 40% and comprises a double-stranded RNA, wherein the double-stranded RNA is either blunt ended or has a length of 14 to 25 nucleotides, and wherein said highly conserved domain sequence is located in nucleotides from 241 to 263 of SEQ ID NO: 1.

2. The sliRNA of claim 1, wherein said nucleotide sequence is at least 95% identical to said fragment of the highly conserved domain.

3. The sliRNA of claim 1, wherein said nucleotide sequence is 100% identical to said fragment of the highly conserved domain.

4. The sliRNA of claim 1, wherein said Toll-like Receptor is Toll-like Receptor 3 (TLR3).

5. The sliRNA of claim 1, wherein said picornavirus is a human virus selected from the group consisting of: poliovirus, coxsackievirus, and echovirus.

6. The sliRNA of claim 1, wherein said picornavirus is an enterovirus.

7. The sliRNA of claim 1, wherein said double stranded RNA is blunt ended.

8. The sliRNA of claim 1, wherein said sliRNA has a length of 14 to 25 nucleotides.

9. The sliRNA of claim 1, wherein said sliRNA comprises 1 to 2 bases of DNA adjacent to the 3'-end of said nucleotide sequence.

10. The sliRNA of claim 1, comprising a double-stranded RNA molecule having the sequences:

```
Sense:
                                      (SEQ ID NO: 14)
5'-UAGGU ACUUCGAGAAGCCUAGU ANn-3'

Antisense:
                                      (SEQ ID NO: 15)
5'-UACUAGGCUUCUCGAAGUACCUANn-3',
```

wherein n is 1 or 2, and at least one N is uridine (U).

11. The sliRNA of claim 1, comprising a double-stranded RNA molecule having the sequences:

```
Sense:
                                 (SEQ ID NO: 28)
5'-AGGUACUUCGAGAAGCCNn-3'

Antisense:
                                 (SEQ ID NO: 29)
5'-GGCUUCUCGAAGUACCUNn-3',
```

wherein N is a nucleoside, which can be cytidine (C), guanosine (G), adenosine (A), uridine (U), deoxycytidine (dC), deoxyguanosine (dG), deoxyadenosine (dA), or deoxythymidine (dT), and wherein n is an integer from 0 to 2.

12. The sliRNA of claim 10, wherein n is 2, and one N is dT and the other N is U.

13. The sliRNA of claim 11, wherein the N is dT and n is 2.

14. A pharmaceutical composition, comprising the sliRNA of claim 1, and a pharmaceutical acceptable carrier.

15. A method for treating a choroidal neovascularization-related disease, comprising administering a pharmaceutically effective amount of the sliRNA of claim 1 to a subject in need of such treatment.

16. The method of claim 15, wherein said disease is selected from the group consisting of: age-related macular degeneration (AMD) and diabetic retinopathy.

17. The sliRNA of claim 1, wherein the sliRNA has a GC content of 40%-60%.

* * * * *

SEQUENCE LISTING

```
<160> NUMBER OF SEQ ID NOS: 33

<210> SEQ ID NO 1
<211> LENGTH: 644
<212> TYPE: DNA
<213> ORGANISM: enterovirus

<400> SEQUENCE: 1

ttaaaacagc tctggggttg ttcccacccc agaggcccac gtggcggcta gtactccggt     60

accccggtac ccttgtacgc ctgttttata ctccctttcc caagtaactt tagaagaaat    120

aaactaatgt tcaacaggag ggggtacaaa ccagtaccac cacgaacaca cacttctgtt    180

tccccggtga agttgcatag actgtaccca cggttgaaag cgatgaatcc gttacccgct    240

taggtacttc gagaagccta gtatcatctt ggaatcttcg atgcgttgcg atcagcactc    300
```

-continued

```
taccccgagt gtagcttggg tcgatgagtc tggacacccc acaccggcga cggtggtcca    360

ggctgcgttg gcggcctacc catggctagc accatgggac gctagttgtg aacaaggtgc    420

gaagagccta ttgagctacc tgagagtcct ccggcccctg aatgcggcta atcccaacca    480

cggagcaaat gctcacaatc cagtgagtgg tttgtcgtaa tgcgcaagtc tgtggcggaa    540

ccgactactt tgggcgtccg tgtttccttt tatttttatt atggctgctt atggtgacaa    600

tctgagattg ttatcatata gctattggat tagccatccg gtga                     644


<210> SEQ ID NO 2
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2

uagguacuuc gagaagccua gua                                             23


<210> SEQ ID NO 3
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3

uacuaggcuu cucgaaguac cua                                             23


<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4

caaugcauug agaggccugg autt                                            24


<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5

auccaggccu cucaaugcau ugtt                                            24


<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

-continued

<223> OTHER INFORMATION: Description of Combined DNA/RNA Molecule:
      Synthetic oligonucleotide

<400> SEQUENCE: 6
uagguacuuc gagaagccua guatt 25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
uacuaggcuu cucgaaguac cuatt 25

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
ccugagaguc cuccggcccc utt 23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
aggggccgga ggacucucag gtt 23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
agagagaaag uagagaaggg ctt 23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide -continued

```
<220> FEATURE:
<223> OTHER INFORMATION: Description of Combined DNA/RNA Molecule:
      Synthetic oligonucleotide

<400> SEQUENCE: 11

gcccuucucu acuuucucuc utt                                          23


<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12

uaggaaccca agaaccccuc ctt                                          23


<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13

ggagggguuc uuggguuccu att                                          23


<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (24)..(25)
<223> OTHER INFORMATION: Cytosine, guanine, adenine, and thymine, or the
      deoxygen forms thereof
<220> FEATURE:
<221> NAME/KEY: misc_feature
<222> LOCATION: (24)..(25)
<223> OTHER INFORMATION: This region may encompass 0-2 repeating 'N'
      bases

<400> SEQUENCE: 14

uagguacuuc gagaagccua guann                                        25


<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
```

-continued

```
<222> LOCATION: (24)..(25)
<223> OTHER INFORMATION: Cytosine, guanine, adenine, and thymine, or the
      deoxygen forms thereof
<220> FEATURE:
<221> NAME/KEY: misc_feature
<222> LOCATION: (24)..(25)
<223> OTHER INFORMATION: This region may encompass 0-2 repeating 'N'
      bases

<400> SEQUENCE: 15

uacuaggcuu cucgaaguac cuann                                          25


<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16

taggtacttc gagaagccta gtatt                                          25


<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17

uacuaggcuu cucgaaguac cuatt                                          25


<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18

caatgcattg agaggcctgg attt                                           24


<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

atccaggcct ctcaatgcat tgtt                                           24


<210> SEQ ID NO 20
<211> LENGTH: 23
<212> TYPE: DNA
<213> ORGANISM: Artificial Sequence
```

<220> FEATURE:
<223> OTHER INFORMATION: Description of Artificial Sequence: Synthetic
primer

<400> SEQUENCE: 20
ctggaactac acaagaacga gag 23

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21
cttcaagtcc tcatagatgc tacc 24

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 22
tttagagtcc aacggcttag 20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 23
tggaggttca gtgaccttag 20

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 24
gacatcttcc aggagtacc 19

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
tgctgtagga agctcatctc 20

<210> SEQ ID NO 26
<211> LENGTH: 22
<212> TYPE: DNA
<213> ORGANISM: Artificial Sequence
<220> FEATURE:

-continued

<223> OTHER INFORMATION: Description of Artificial Sequence: Synthetic
      primer

<400> SEQUENCE: 26
gtatgactcc actcacggca aa                                             22

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtctcgctc ctggaagatg                                                20

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(19)
<223> OTHER INFORMATION: Cytosine, guanine, adenine, and thymine, or the
      deoxygen forms thereof
<220> FEATURE:
<221> NAME/KEY: misc_feature
<222> LOCATION: (18)..(19)
<223> OTHER INFORMATION: This region may encompass 0-2 repeating 'N'
      bases

<400> SEQUENCE: 28
agguacuucg agaagccnn                                                 19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(19)
<223> OTHER INFORMATION: Cytosine, guanine, adenine, and thymine, or the
      deoxygen forms thereof
<220> FEATURE:
<221> NAME/KEY: misc_feature
<222> LOCATION: (18)..(19)
<223> OTHER INFORMATION: This region may encompass 0-2 repeating 'N'
      bases

<400> SEQUENCE: 29
ggcuucucga aguaccunn                                                 19

<210> SEQ ID NO 30
<211> LENGTH: 17
<212> TYPE: RNA
<213> ORGANISM: Artificial Sequence
<220> FEATURE:
<223> OTHER INFORMATION: Description of Artificial Sequence: Synthetic -continued

```
      oligonucleotide

<400> SEQUENCE: 30

agguacuucg agaagcc                                                 17


<210> SEQ ID NO 31
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31

ggcuucucga aguaccu                                                 17


<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32

agguacuucg agaagcctt                                               19


<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33

ggcuucucga aguaccutt                                               19
```